US012692313B2

(12) United States Patent
Pulé et al.

(10) Patent No.: US 12,692,313 B2
(45) Date of Patent: Jul. 28, 2026

(54) CHIMERIC ANTIGEN RECEPTOR (CAR) COMPRISING A CD19-BINDING DOMAIN

(71) Applicant: AUTOLUS LIMITED, London (GB)

(72) Inventors: Martin Pulé, London (GB); Leila Mekkaoui, London (GB); Persis Amrolia, London (GB); Sara Ghorashian, London (GB); Anne Kramer, London (GB); Gordon Cheung, London (GB)

(73) Assignee: AUTOLUS LIMITED, London (GB)

( * ) Notice: Subject to any disclaimer, the term of this patent is extended or adjusted under 35 U.S.C. 154(b) by 724 days.

(21) Appl. No.: 18/153,990

(22) Filed: Jan. 12, 2023

(65) Prior Publication Data

US 2023/0220077 A1      Jul. 13, 2023

Related U.S. Application Data

(63) Continuation of application No. 16/573,854, filed on Sep. 17, 2019, now Pat. No. 11,578,126, which is a continuation of application No. 15/555,508, filed as application No. PCT/GB2016/050574 on Mar. 4, 2016, now Pat. No. 10,457,730.

(30) Foreign Application Priority Data

Mar. 5, 2015     (GB) ..................................... 1503742

(51) Int. Cl.
| | |
|---|---|
| *A61K 40/31* | (2025.01) |
| *A61K 40/11* | (2025.01) |
| *A61K 40/42* | (2025.01) |
| *C07K 14/705* | (2006.01) |
| *C07K 16/28* | (2006.01) |
| *C07K 16/30* | (2006.01) |
| *C12N 5/0783* | (2010.01) |

(52) U.S. Cl.
CPC .......... *C07K 16/2803* (2013.01); *A61K 40/11* (2025.01); *A61K 40/31* (2025.01); *A61K 40/4211* (2025.01); *C07K 14/7051* (2013.01); *C07K 14/70517* (2013.01); *C07K 14/70521* (2013.01); *C07K 14/70578* (2013.01); *C07K 14/70596* (2013.01); *C07K 16/3061* (2013.01); *C12N 5/0636* (2013.01); *A61K 2239/31* (2023.05); *A61K 2239/38* (2023.05); *A61K 2239/48* (2023.05); *C07K 2317/56* (2013.01); *C07K 2317/565* (2013.01); *C07K 2317/567* (2013.01); *C07K 2317/622* (2013.01); *C07K 2317/73* (2013.01); *C07K 2319/03* (2013.01); *C07K 2319/33* (2013.01); *C07K 2319/74* (2013.01); *C12N 2510/00* (2013.01); *C12N 2740/15043* (2013.01)

(58) Field of Classification Search
None
See application file for complete search history.

(56) References Cited

U.S. PATENT DOCUMENTS

| | | | | |
|---|---|---|---|---|
| 10,098,926 | B2 | 10/2018 | Pulé et al. | |
| 10,174,099 | B2 | 1/2019 | Pulé et al. | |
| 10,457,730 | B2 | 10/2019 | Pulé et al. | |
| 10,981,970 | B2 | 4/2021 | Pulé et al. | |
| 11,034,750 | B2 | 6/2021 | Pule et al. | |
| 11,091,532 | B2 | 8/2021 | Pule et al. | |
| 2017/0066838 | A1* | 3/2017 | Pulé ................... | C07K 16/3084 |
| 2017/0369550 | A1 | 12/2017 | Pule et al. | |
| 2018/0371054 | A1 | 12/2018 | Pule et al. | |
| 2019/0161531 | A1 | 5/2019 | Pulé et al. | |
| 2023/0019650 | A1* | 1/2023 | Pulé ........................ | G16H 50/30 |
| 2023/0027993 | A1* | 1/2023 | Pulé ........................ | A61K 40/31 |
| 2024/0301088 | A1* | 9/2024 | Pulé ................... | C07K 14/7051 |
| 2024/0374727 | A1* | 11/2024 | Mansour .............. | C12N 5/0636 |
| 2024/0408134 | A1* | 12/2024 | Srivastava ............. | C07K 14/71 |
| 2025/0268941 | A1* | 8/2025 | Pulé ................... | A61K 40/4211 |
| 2025/0289891 | A1* | 9/2025 | Kinna .................. | A61K 40/421 |

FOREIGN PATENT DOCUMENTS

| | | | |
|---|---|---|---|
| CN | 102421800 A | 4/2012 | |
| CN | 104159909 A | 11/2014 | |
| WO | WO-2010/095031 A2 | 8/2010 | |

(Continued)

OTHER PUBLICATIONS

Amrolia et al., Chimeric Antigen Receptor T Cells for ALL, Lancet, Feb. 7, 2015, vol. 385, pp. 488-490.

Brentjens, et al., CD19-targeted T cells rapidly induce molecular remissions in adults with chemotherapy-refractory acute lymphoblastic leukemia, Sci. Transl. Med., 5:177ra38 (2013).

Davila et al., "Efficacy and Toxicity Management of 19-28z CAR T Cell Therapy in B Cell Acute Lymphoblastic Leukemia," Sci. Translat. Med. 6:224RA24 (2014).

Day et al., PD-1 expression on HIV-specific T cells is associated with T-cell exhaustion and disease progression, Nature, 443:350-4 (2006).

EPO Communication Pursuant to Rule 161(1) and 162 EPC dated Oct. 17, 2017 in EP 16709529.8.

EPO Rule 71(3) Communication dated Nov. 9, 2018 in EP 16709529.8.

(Continued)

*Primary Examiner* — Michail A Belyavskyi

(74) *Attorney, Agent, or Firm* — MARSHALL, GERSTEIN & BORUN LLP

(57) ABSTRACT

There is provided a chimeric antigen receptor (CAR) comprising a CD19-binding domain which comprises a) a heavy chain variable region (VH) having complementarity determining regions (CDRs) with the following sequences: CDR1—GY-AFSSS (SEQ ID No. 1); CDR2—YPGDED (SEQ ID No. 2) CDR3—SLLYGDYLDY (SEQ ID No. 3); and b) a light chain variable region (VL) having CDRs with the following sequences: CDR1—SASSSVSYMH (SEQ ID No. 4); CDR2—DTSKLAS (SEQ ID No. 5) CDR3—QQWNINPLT (SEQ ID No. 6). There is also provided a cell comprising such a CAR, and the use of such a cell in the treatment of cancer, in particular a B cell malignancy.

15 Claims, 11 Drawing Sheets

Specification includes a Sequence Listing.

(56)            References Cited

FOREIGN PATENT DOCUMENTS

WO     WO-2013/126712 A1     8/2013
WO     WO-2014/184143 A1     11/2014

OTHER PUBLICATIONS

Ghorashian et al., A novel low affinity CD19CAR results in durable disease remissions and prolonged CAR T cell persistence without severe CRS or neurotoxicity in patients with paediatric ALL, *Blood*, 130(806):1-5 (2007).

Guedan et al., Enhancing CAR T cell persistence through ICOS and 4-1BB costimulation., *JCL Insight*, . doi: 10.1172/jci.insight.96976 (2018).

Imai et al., Chimeric receptors with 4-1BB signaling capacity provoke potent cytotoxicity against acute lymphoblastic leukemia, Leuk., 18:676-84 (2004).

International Preliminary Report on Patentability, PCT/GB2016/050574, dated Sep. 5, 2017.

International Search Report and Written Opinion for PCT/GB2016/050574 (May 20, 2016).

Kochenderfer et al., Chemotherapy-Refractory Diffuse Large B-Cell Lymphoma and Indolent B-Cell Malignancies., J. Clin Oncol. 33:540-549 (2015).

Kochenderfer et al., Construction and Pre-clinical Evaluation of an Anti-CD19 Chimeric Antigen Receptor, J. Immunother., 2009, vol. 32, No. 7, pp. 689-702.

Lee et al., T cells expressing CD19 chimeric antigen receptors for acute lymphoblastic leukaemia in children and young adults: a phase 1 dose-escalation trial, Lancets, 385(9967):517-28 (2015).

Lichtman et al., Chimeric Antigen receptor T-Cells for B-Cell malignancies, *Trans. Res.*, 187:59-82 (2017).

Long et al., 4-1BB costimulation ameliorates T cell exhaustion induced by tonic signaling of chimeric antigen receiptors, *Nature Med.*, 21(6):581-90 (2015).

López-Alvarez et al., Association of monoclonal expansion of Epstein-Barr virus-negative CD158a+ NK cells secreting large amounts of gamma interferon with hemophagocytic lymphohistiocytosis, Clin. Vaccine Immunol., 16(1):142-5 (2009).

Maude et al., "Chimeric Antigen Receptor T Cells for Sustained Remissions in Leukemia," New Engl. J. Med. 371:1507-1517 (2014).

Qasim et al., Preliminary results for UCART19, an allogenic antiCD19 CAR T-cell product in a first-in-human trial (PALL) in pediatric patients with CD19+ relapsed/refractory B-cell acute lymphoblastic leukemia, *Blood*, 130(127):1-4 (2017).

\* cited by examiner (a)

Figure 1:
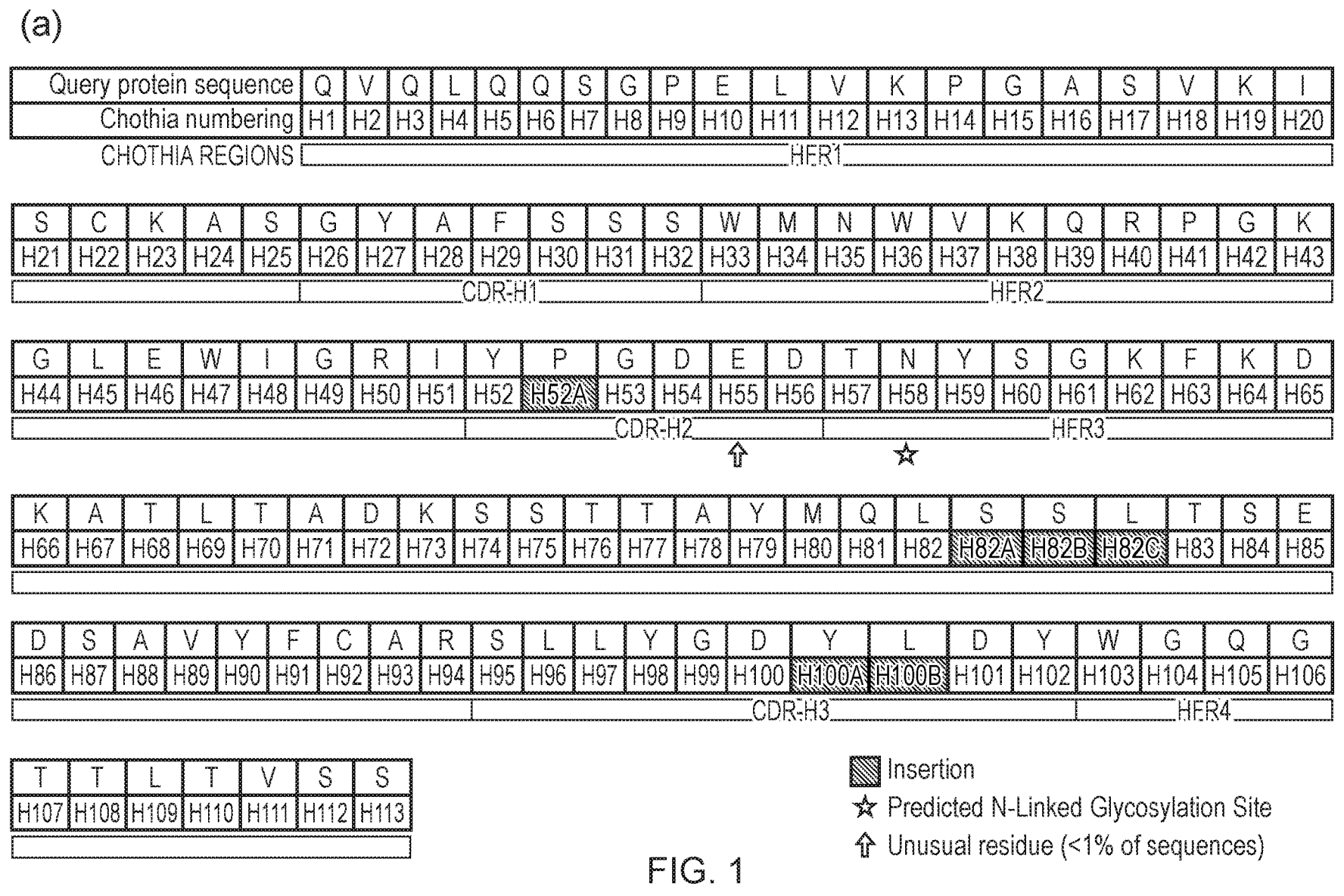

| Query protein sequence | Q | V | Q | L | Q | Q | S | G | P | E | L | V | K | P | G | A | S | V | K | I |
|---|---|---|---|---|---|---|---|---|---|---|---|---|---|---|---|---|---|---|---|---|
| Chothia numbering | H1 | H2 | H3 | H4 | H5 | H6 | H7 | H8 | H9 | H10 | H11 | H12 | H13 | H14 | H15 | H16 | H17 | H18 | H19 | H20 |

CHOTHIA REGIONS: HFR1

| | S | C | K | A | S | G | Y | A | F | S | S | Y | W | M | N | W | V | K | Q | R | P | G | K |
|---|---|---|---|---|---|---|---|---|---|---|---|---|---|---|---|---|---|---|---|---|---|---|---|
| | H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |

CDR-H1   HFR2

| | G | L | E | W | I | G | R | I | Y | P | G | D | E | D | T | N | Y | S | G | K | F | K | D |
|---|---|---|---|---|---|---|---|---|---|---|---|---|---|---|---|---|---|---|---|---|---|---|---|
| | H44 | H45 | H46 | H47 | H48 | H49 | H50 | H51 | H52 | H52A | H53 | H54 | H55 | H56 | H57 | H58 | H59 | H60 | H61 | H62 | H63 | H64 | H65 |

CDR-H2   HFR3

| | K | A | T | L | T | A | D | K | S | S | S | T | A | Y | M | Q | L | S | S | L | T | S | E |
|---|---|---|---|---|---|---|---|---|---|---|---|---|---|---|---|---|---|---|---|---|---|---|---|
| | H66 | H67 | H68 | H69 | H70 | H71 | H72 | H73 | H74 | H75 | H76 | H77 | H78 | H79 | H80 | H81 | H82 | H82A | H82B | H82C | H83 | H84 | H85 |

| | D | S | A | V | Y | F | C | A | R | S | L | L | Y | G | D | Y | L | D | Y | W | G | Q | G |
|---|---|---|---|---|---|---|---|---|---|---|---|---|---|---|---|---|---|---|---|---|---|---|---|
| | H86 | H87 | H88 | H89 | H90 | H91 | H92 | H93 | H94 | H95 | H96 | H97 | H98 | H99 | H100 | H100A | H100B | H101 | H102 | H103 | H104 | H105 | H106 |

CDR-H3   HFR4

| | T | T | L | T | V | S | S |
|---|---|---|---|---|---|---|---|
| | H107 | H108 | H109 | H110 | H111 | H112 | H113 |

Legend:

▨ Insertion
☆ Predicted N-Linked Glycosylation Site
⇧ Unusual residue (<1% of sequences)

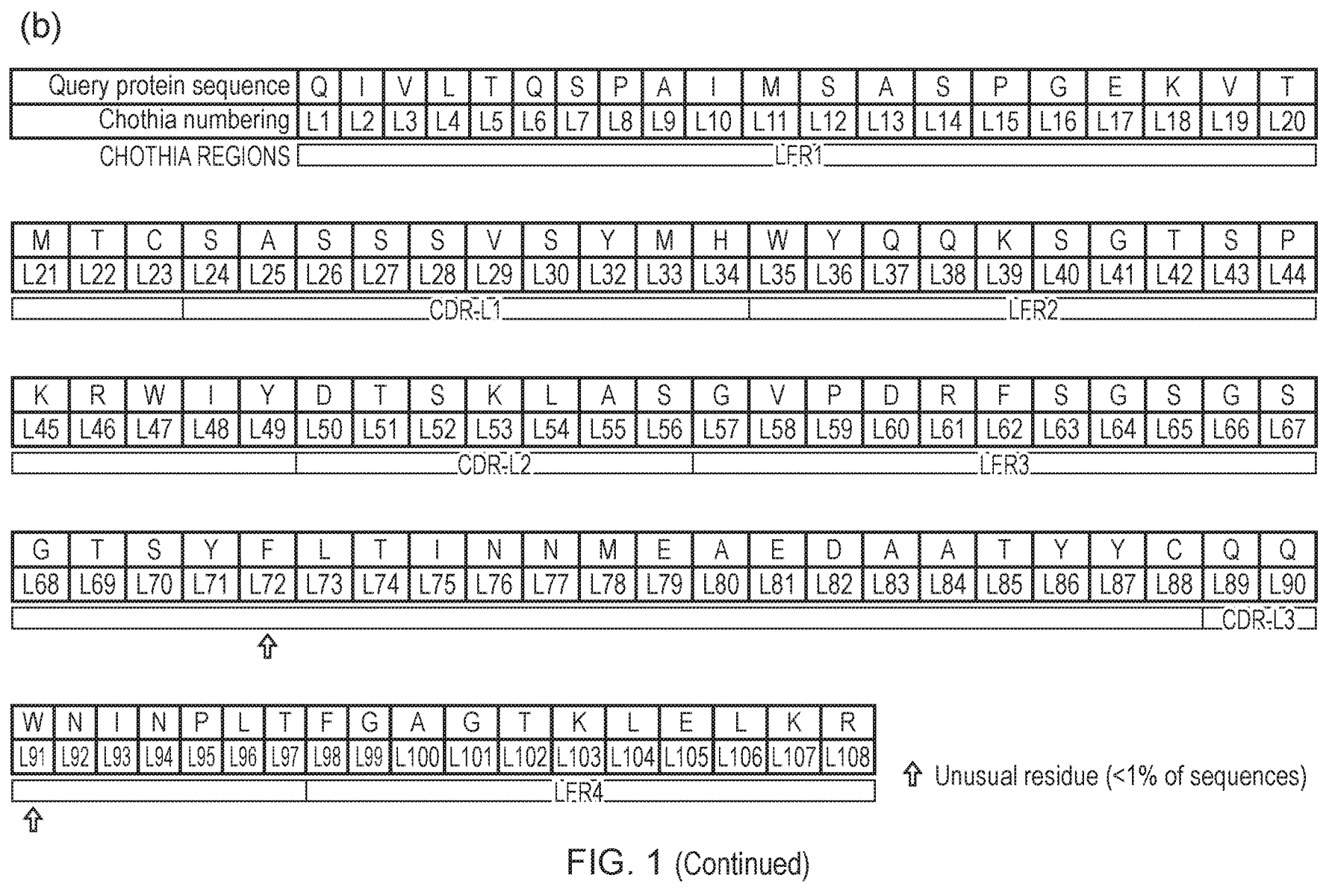

| Query protein sequence | Q | I | V | L | T | Q | S | P | A | I | M | S | A | S | P | G | E | K | V | T |
|---|---|---|---|---|---|---|---|---|---|---|---|---|---|---|---|---|---|---|---|---|
| Chothia numbering | L1 | L2 | L3 | L4 | L5 | L6 | L7 | L8 | L9 | L10 | L11 | L12 | L13 | L14 | L15 | L16 | L17 | L18 | L19 | L20 |

CHOTHIA REGIONS: LFR1

| M | T | C | S | A | S | S | S | V | S | Y | M | H | W | Y | Q | Q | K | S | G | T | S | S | P |
|---|---|---|---|---|---|---|---|---|---|---|---|---|---|---|---|---|---|---|---|---|---|---|---|
| L21 | L22 | L23 | L24 | L25 | L26 | L27 | L28 | L29 | L30 | L31 | L32 | L33 | L34 | L35 | L36 | L37 | L38 | L39 | L40 | L41 | L42 | L43 | L44 |

CDR-L1 — LFR2

| K | R | W | I | Y | D | T | S | K | L | A | S | G | V | P | D | R | F | S | G | S | G | S |
|---|---|---|---|---|---|---|---|---|---|---|---|---|---|---|---|---|---|---|---|---|---|---|
| L45 | L46 | L47 | L48 | L49 | L50 | L51 | L52 | L53 | L54 | L55 | L56 | L57 | L58 | L59 | L60 | L61 | L62 | L63 | L64 | L65 | L66 | L67 |

CDR-L2 — LFR3

| G | T | S | Y | F | L | T | I | I | N | N | M | E | A | E | D | A | A | T | Y | Y | C | Q | Q |
|---|---|---|---|---|---|---|---|---|---|---|---|---|---|---|---|---|---|---|---|---|---|---|---|---|
| L68 | L69 | L70 | L71 | L72 | L73 | L74 | L75 | L76 | L77 | L78 | L79 | L80 | L81 | L82 | L83 | L84 | L85 | L86 | L87 | L88 | L89 | L90 | |

LFR3 — CDR-L3

| W | N | I | N | P | L | T | F | G | A | G | T | K | L | E | L | K | R |
|---|---|---|---|---|---|---|---|---|---|---|---|---|---|---|---|---|---|
| L91 | L92 | L93 | L94 | L95 | L96 | L97 | L98 | L99 | L100 | L101 | L102 | L103 | L104 | L105 | L106 | L107 | L108 |

CDR-L3 — LFR4

⇧ (unusual residue markers at L91, L92)

⇧ Unusual residue (<1% of sequences)

FIG. 1 (Continued)

(a)
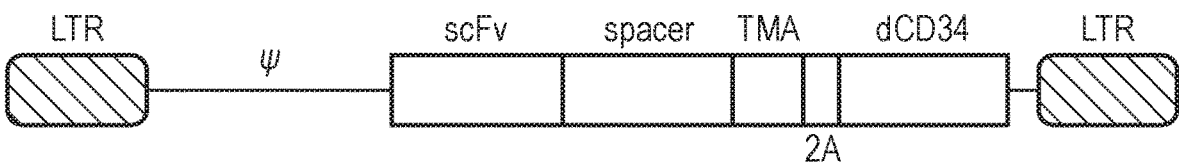
(b)
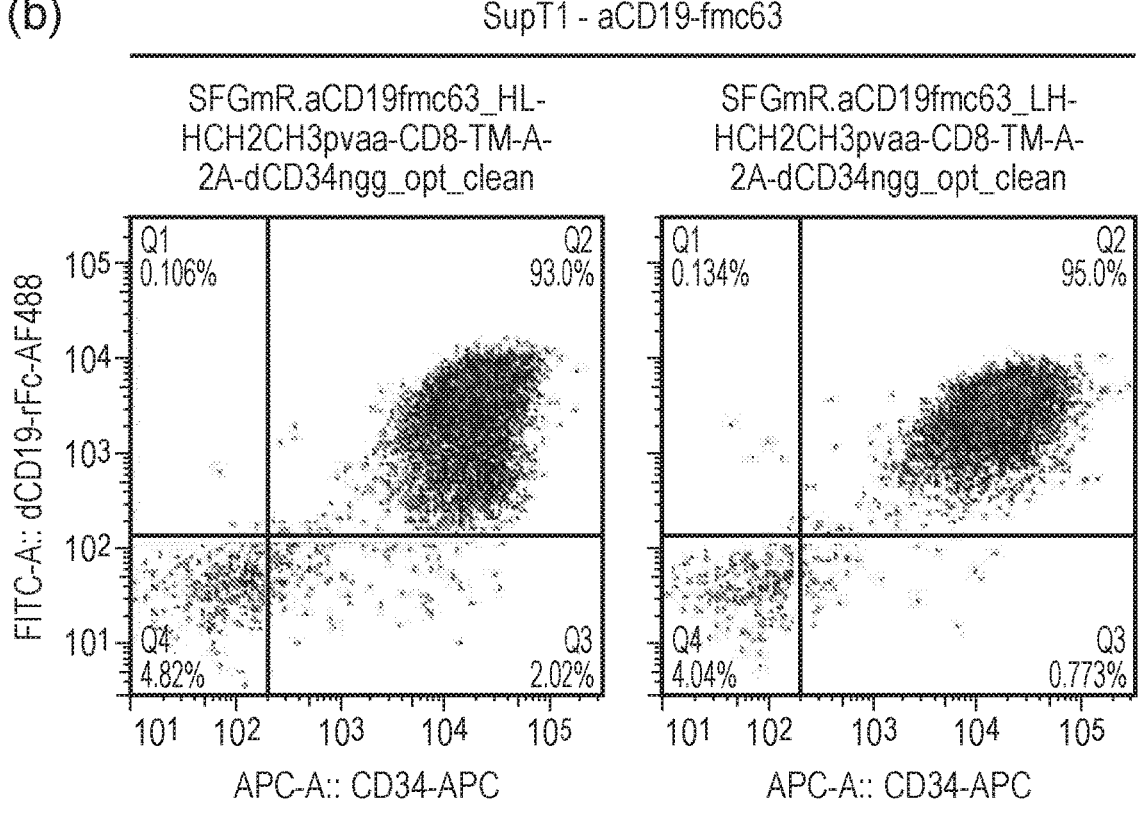
FIG. 3

(e)

(c)
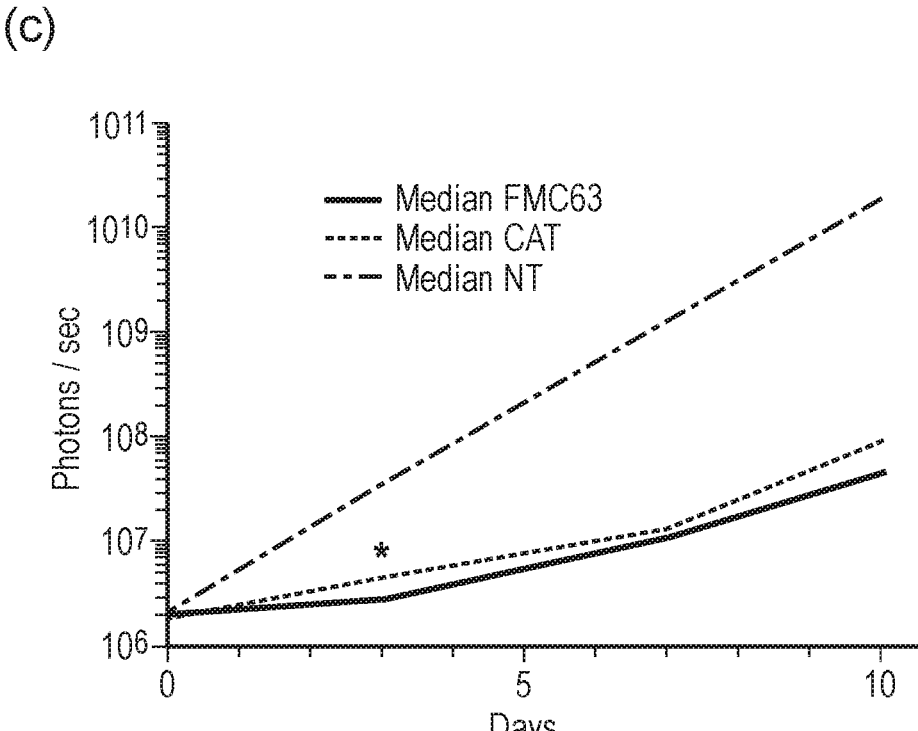
(d)
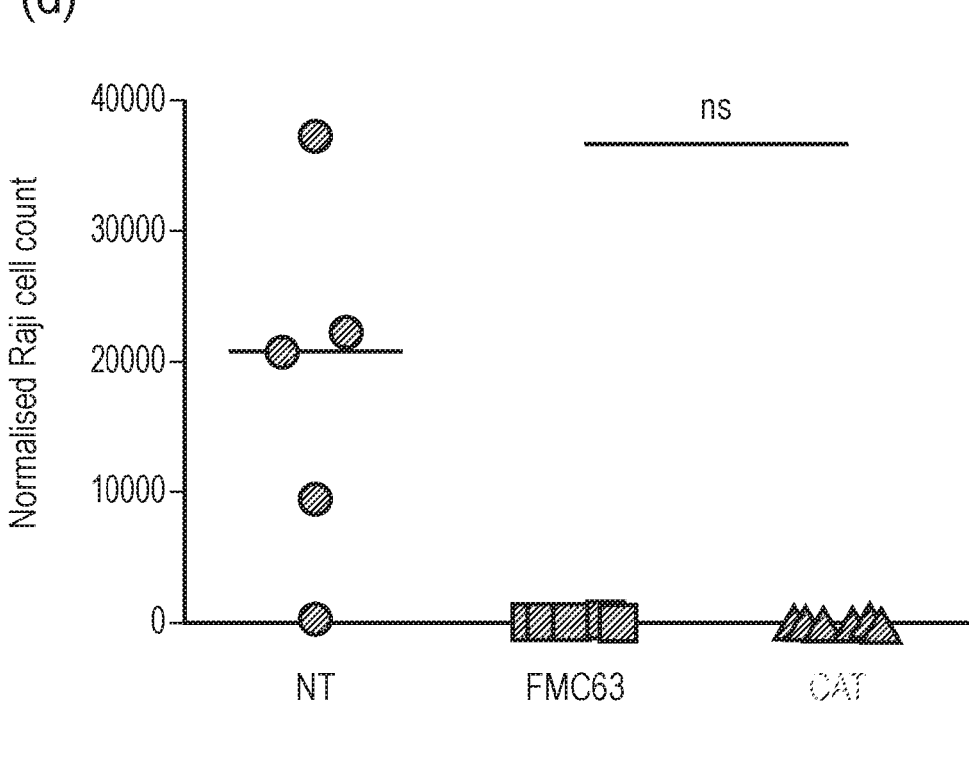
FIG. 6 (Continued)

SEQUENCE LISTING

```
Sequence total quantity: 43
SEQ ID NO: 1            moltype = AA  length = 7
FEATURE                 Location/Qualifiers
REGION                  1..7
                        note = heavy chain variable region (VH) complementarity
                         determining region (CDR) CDR1
source                  1..7
                        mol_type = protein
                        organism = synthetic construct
SEQUENCE: 1
GYAFSSS                                                          7

SEQ ID NO: 2            moltype = AA  length = 6
FEATURE                 Location/Qualifiers
REGION                  1..6
                        note = VH CDR, CDR2
source                  1..6
                        mol_type = protein
```

-continued

```
                        organism = synthetic construct
SEQUENCE: 2
YPGDED                                                              6

SEQ ID NO: 3           moltype = AA   length = 10
FEATURE                Location/Qualifiers
REGION                 1..10
                       note = VH CDR, CDR3
source                 1..10
                       mol_type = protein
                       organism = synthetic construct
SEQUENCE: 3
SLLYGDYLDY                                                          10

SEQ ID NO: 4           moltype = AA   length = 10
FEATURE                Location/Qualifiers
REGION                 1..10
                       note = light chain variable region (VL) CDR, CDR1
source                 1..10
                       mol_type = protein
                       organism = synthetic construct
SEQUENCE: 4
SASSSVSYMH                                                          10

SEQ ID NO: 5           moltype = AA   length = 7
FEATURE                Location/Qualifiers
REGION                 1..7
                       note = VL CDR, CDR2
source                 1..7
                       mol_type = protein
                       organism = synthetic construct
SEQUENCE: 5
DTSKLAS                                                             7

SEQ ID NO: 6           moltype = AA   length = 9
FEATURE                Location/Qualifiers
REGION                 1..9
                       note = VL CDR, CDR3
source                 1..9
                       mol_type = protein
                       organism = synthetic construct
SEQUENCE: 6
QQWNINPLT                                                           9

SEQ ID NO: 7           moltype = AA   length = 119
FEATURE                Location/Qualifiers
REGION                 1..119
                       note = VH sequence from murine monoclonal antibody
source                 1..119
                       mol_type = protein
                       organism = synthetic construct
SEQUENCE: 7
QVQLQQSGPE LVKPGASVKI SCKASGYAFS SSWMNWVKQR PGKGLEWIGR IYPGDEDTNY   60
SGKFKDKATL TADKSSTTAY MQLSSLTSED SAVYFCARSL LYGDYLDYWG QGTTLTVSS    119

SEQ ID NO: 8           moltype = AA   length = 107
FEATURE                Location/Qualifiers
REGION                 1..107
                       note = VL sequence from murine monoclonal antibody
source                 1..107
                       mol_type = protein
                       organism = synthetic construct
SEQUENCE: 8
QIVLTQSPAI MSASPGEKVT MTCSASSVS YMHWYQQKSG TSPKRWIYDT SKLASGVPDR    60
FSGSGSGTSY FLTINNMEAE DAATYYCQQW NINPLTFGAG TKLELKR                 107

SEQ ID NO: 9           moltype = AA   length = 241
FEATURE                Location/Qualifiers
REGION                 1..241
                       note = VH-VL scFv sequence from murine monoclonal antibody
source                 1..241
                       mol_type = protein
                       organism = synthetic construct
SEQUENCE: 9
QVQLQQSGPE LVKPGASVKI SCKASGYAFS SSWMNWVKQR PGKGLEWIGR IYPGDEDTNY   60
SGKFKDKATL TADKSSTTAY MQLSSLTSED SAVYFCARSL LYGDYLDYWG QGTTLTVSSG   120
GGGSGGGGSG GGGSQIVLTQ SPAIMSASPG EKVTMTCSAS SSVSYMHWYQ QKSGTSPKRW   180
IYDTSKLASG VPDRFSGSGS GTSYFLTINN MEAEDAATYY CQQWNINPLT FGAGTKLELK   240
R                                                                   241
```

-continued

```
SEQ ID NO: 10              moltype = AA   length = 488
FEATURE                    Location/Qualifiers
REGION                     1..488
                           note = CAT19 chimeric antigen receptor (CAR) using
                           "Campana" architecture
source                     1..488
                           mol_type = protein
                           organism = synthetic construct
SEQUENCE: 10
MGTSLLCWMA LCLLGADHAD AQVQLQQSGP ELVKPGASVK ISCKASGYAF SSSWMNWVKQ  60
RPGKGLEWIG RIYPGDEDTN YSGKFKDKAT LTADKSSTTA YMQLSSLTSE DSAVYFCARS  120
LLYGDYLDYW GQGTTLTVSS GGGGSGGGGS GGGGSQIVLT QSPAIMSASP GEKVTMTCSA  180
SSSVSYMHWY QQKSGTSPKR WIYDTSKLAS GVPDRFSGSG SGTSYFLTIN NMEAEDAATY  240
YCQQWNINPL TFGAGTKLEL KRSDPTTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYQ QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                          488

SEQ ID NO: 11              moltype = AA   length = 483
FEATURE                    Location/Qualifiers
REGION                     1..483
                           note = CAT19 CAR with an OX40-Zeta endodomain
source                     1..483
                           mol_type = protein
                           organism = synthetic construct
SEQUENCE: 11
MGTSLLCWMA LCLLGADHAD AQVQLQQSGP ELVKPGASVK ISCKASGYAF SSSWMNWVKQ  60
RPGKGLEWIG RIYPGDEDTN YSGKFKDKAT LTADKSSTTA YMQLSSLTSE DSAVYFCARS  120
LLYGDYLDYW GQGTTLTVSS GGGGSGGGGS GGGGSQIVLT QSPAIMSASP GEKVTMTCSA  180
SSSVSYMHWY QQKSGTSPKR WIYDTSKLAS GVPDRFSGSG SGTSYFLTIN NMEAEDAATY  240
YCQQWNINPL TFGAGTKLEL KRSDPTTTPA PRPPTPAPTI ASQPLSLRPE ACRPAAGGAV  300
HTRGLDFACD IYIWAPLAGT CGVLLLSLVI TLYCRRDQRL PPDAHKPPGG GSFRTPIQEE  360
QADAHSTLAK IRVKFSRSAD APAYQQGQNQ LYNELNLGRR EEYDVLDKRR GRDPEMGGKP  420
RRKNPQEGLY NELQKDKMAE AYSEIGMKGE RRRGKGHDGL YQGLSTATKD TYDALHMQAL  480
PPR                                                               483

SEQ ID NO: 12              moltype = AA   length = 487
FEATURE                    Location/Qualifiers
REGION                     1..487
                           note = CAT19 CAR with a CD28-Zeta endodomain
source                     1..487
                           mol_type = protein
                           organism = synthetic construct
SEQUENCE: 12
MGTSLLCWMA LCLLGADHAD AQVQLQQSGP ELVKPGASVK ISCKASGYAF SSSWMNWVKQ  60
RPGKGLEWIG RIYPGDEDTN YSGKFKDKAT LTADKSSTTA YMQLSSLTSE DSAVYFCARS  120
LLYGDYLDYW GQGTTLTVSS GGGGSGGGGS GGGGSQIVLT QSPAIMSASP GEKVTMTCSA  180
SSSVSYMHWY QQKSGTSPKR WIYDTSKLAS GVPDRFSGSG SGTSYFLTIN NMEAEDAATY  240
YCQQWNINPL TFGAGTKLEL KRSDPTTTPA PRPPTPAPTI ASQPLSLRPE ACRPAAGGAV  300
HTRGLDFACD IYIWAPLAGT CGVLLLSLVI TLYCRSKRSR LLHSDYMNMT PRRPGPTRKH  360
YQPYAPPRDF AAYRSRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
MQALPPR                                                           487

SEQ ID NO: 13              moltype = AA   length = 527
FEATURE                    Location/Qualifiers
REGION                     1..527
                           note = Third generation CD19 CAR
source                     1..527
                           mol_type = protein
                           organism = synthetic construct
SEQUENCE: 13
MGTSLLCWMA LCLLGADHAD AQVQLQQSGP ELVKPGASVK ISCKASGYAF SSSWMNWVKQ  60
RPGKGLEWIG RIYPGDEDTN YSGKFKDKAT LTADKSSTTA YMQLSSLTSE DSAVYFCARS  120
LLYGDYLDYW GQGTTLTVSS GGGGSGGGGS GGGGSQIVLT QSPAIMSASP GEKVTMTCSA  180
SSSVSYMHWY QQKSGTSPKR WIYDTSKLAS GVPDRFSGSG SGTSYFLTIN NMEAEDAATY  240
YCQQWNINPL TFGAGTKLEL KRSDPTTTPA PRPPTPAPTI ASQPLSLRPE ACRPAAGGAV  300
HTRGLDFACD IFWVLVVVGG VLACYSLLVT VAFIIFWVRS KRSRLLHSDY MNMTPRRPGP  360
TRKHYQPYAP PRDFAAYRSR DQRLPPDAHK PPGGGSFRTP IQEEQADAHS TLAKIRVKFS  420
RSADAPAYQQ GQNQLYNELN LGRREEYDVL DKRRGRDPEM GGKPRRKNPQ EGLYNELQKD  480
KMAEAYSEIG MKGERRRGKG HDGLYQGLST ATKDTYDALH MQALPPR               527

SEQ ID NO: 14              moltype = AA   length = 465
FEATURE                    Location/Qualifiers
REGION                     1..465
                           note = CD19 CAR with IgG1 hinge spacer
source                     1..465
```

```
                              mol_type = protein
                              organism = synthetic construct
SEQUENCE: 14
MGTSLLCWMA LCLLGADHAD AQVQLQQSGP ELVKPGASVK ISCKASGYAF SSSWMNWVKQ    60
RPGKGLEWIG RIYPGDEDTN YSGKFKDKAT LTADKSSTTA YMQLSSLTSE DSAVYFCARS   120
LLYGDYLDYW GQGTTLTVSS GGGGSGGGGS GGGGSQIVLT QSPAIMSASP GEKVTMTCSA   180
SSSVSYMHWY QQKSGTSPKR WIYDTSKLAS GVPDRFSGSG SGTSYFLTIN NMEAEDAATY   240
YCQQWNINPL TFGAGTKLEL KRSDPAEPKS PDKTHTCPPC PKDPKFWVLV VVGGVLACYS   300
LLVTVAFIIF WVRSKRSRLL HSDYMNMTPR RPGPTRKHYQ PYAPPRDFAA YRSRVKFSRS   360
ADAPAYQQGQ NQLYNELNLG RREEYDVLDK RRGRDPEMGG KPRRKNPQEG LYNELQKDKM   420
AEAYSEIGMK GERRRGKGHD GLYQGLSTAT KDTYDALHMQ ALPPR                   465

SEQ ID NO: 15               moltype = AA  length = 681
FEATURE                     Location/Qualifiers
REGION                      1..681
                            note = CD19 CAR with hinge-CH2-CH3 of human IgG1, FcR
                             binding sites mutated out
source                      1..681
                            mol_type = protein
                            organism = synthetic construct
SEQUENCE: 15
MGTSLLCWMA LCLLGADHAD AQVQLQQSGP ELVKPGASVK ISCKASGYAF SSSWMNWVKQ    60
RPGKGLEWIG RIYPGDEDTN YSGKFKDKAT LTADKSSTTA YMQLSSLTSE DSAVYFCARS   120
LLYGDYLDYW GQGTTLTVSS GGGGSGGGGS GGGGSQIVLT QSPAIMSASP GEKVTMTCSA   180
SSSVSYMHWY QQKSGTSPKR WIYDTSKLAS GVPDRFSGSG SGTSYFLTIN NMEAEDAATY   240
YCQQWNINPL TFGAGTKLEL KRSDPAEPKS PDKTHTCPPC PAPPVAGPSV FLFPPKPKDT   300
LMIARTPEVT CVVVDVSHED PEVKFNWYVD GVEVHNAKTK PREEQYNSTY RVVSVLTVLH   360
QDWLNGKEYK CKVSNKALPA PIEKTISKAK GQPREPQVYT LPPSRDELTK NQVSLTCLVK   420
GFYPSDIAVE WESNGQPENN YKTTPPVLDS DGSFFLYSKL TVDKSRWQQG NVFSCSVMHE   480
ALHNHYTQKS LSLSPGKKDP KFWVLVVVGG VLACYSLLVT VAFIIFWVRS KRSRLLHSDY   540
MNMTPRRPGP TRKHYQPYAP PRDFAAYRSR VKFSRSADAP AYQQGQNQLY NELNLGRREE   600
YDVLDKRRGR DPEMGGKPRR KNPQEGLYNE LQKDKMAEAY SEIGMKGERR RGKGHDGLYQ   660
GLSTATKDTY DALHMQALPP R                                           681

SEQ ID NO: 16               moltype = AA  length = 7
FEATURE                     Location/Qualifiers
REGION                      1..7
                            note = VH CDR, CDR1
source                      1..7
                            mol_type = protein
                            organism = synthetic construct
SEQUENCE: 16
GVSLPDY                                                              7

SEQ ID NO: 17               moltype = AA  length = 5
FEATURE                     Location/Qualifiers
REGION                      1..5
                            note = VH CDR, CDR2
source                      1..5
                            mol_type = protein
                            organism = synthetic construct
SEQUENCE: 17
WGSET                                                                5

SEQ ID NO: 18               moltype = AA  length = 12
FEATURE                     Location/Qualifiers
REGION                      1..12
                            note = VH CDR, CDR3
source                      1..12
                            mol_type = protein
                            organism = synthetic construct
SEQUENCE: 18
HYYYGGSYAM DY                                                       12

SEQ ID NO: 19               moltype = AA  length = 11
FEATURE                     Location/Qualifiers
REGION                      1..11
                            note = VL CDR, CDR1
source                      1..11
                            mol_type = protein
                            organism = synthetic construct
SEQUENCE: 19
RASQDISKYL N                                                        11

SEQ ID NO: 20               moltype = AA  length = 7
FEATURE                     Location/Qualifiers
REGION                      1..7
                            note = VL CDR, CDR2
source                      1..7
```

-continued

```
                            mol_type = protein
                            organism = synthetic construct
SEQUENCE: 20
HTSRLHS                                                              7

SEQ ID NO: 21           moltype = AA   length = 9
FEATURE                 Location/Qualifiers
REGION                  1..9
                        note = VL CDR, CDR3
source                  1..9
                        mol_type = protein
                        organism = synthetic construct
SEQUENCE: 21
QQGNTLPYT                                                            9

SEQ ID NO: 22           moltype = AA   length = 27
FEATURE                 Location/Qualifiers
REGION                  1..27
                        note = transmembrane domain
source                  1..27
                        mol_type = protein
                        organism = synthetic construct
SEQUENCE: 22
FWVLVVVGGV LACYSLLVTV AFIIFWV                                        27

SEQ ID NO: 23           moltype = AA   length = 114
FEATURE                 Location/Qualifiers
REGION                  1..114
                        note = CD3 zeta endodomain
source                  1..114
                        mol_type = protein
                        organism = synthetic construct
SEQUENCE: 23
RSRVKFSRSA DAPAYQQGQN QLYNELNLGR REEYDVLDKR RGRDPEMGGK PRRKNPQEGL    60
YNELQKDKMA EAYSEIGMKG ERRRGKGHDG LYQGLSTATK DTYDALHMQA LPPR          114

SEQ ID NO: 24           moltype = AA   length = 42
FEATURE                 Location/Qualifiers
REGION                  1..42
                        note = 41BB endodomain
source                  1..42
                        mol_type = protein
                        organism = synthetic construct
SEQUENCE: 24
KRGRKKLLYI FKQPFMRPVQ TTQEEDGCSC RFPEEEEGGC EL                       42

SEQ ID NO: 25           moltype = AA   length = 37
FEATURE                 Location/Qualifiers
REGION                  1..37
                        note = OX40 endodomain
source                  1..37
                        mol_type = protein
                        organism = synthetic construct
SEQUENCE: 25
RRDQRLPPDA HKPPGGGSFR TPIQEEQADA HSTLAKI                             37

SEQ ID NO: 26           moltype = AA   length = 37
FEATURE                 Location/Qualifiers
REGION                  1..37
                        note = CD28 endodomain
source                  1..37
                        mol_type = protein
                        organism = synthetic construct
SEQUENCE: 26
KRSRLLHSDY MNMTPRRPGP TRKHYQPYAP PRDFAAY                             37

SEQ ID NO: 27           moltype = AA   length = 154
FEATURE                 Location/Qualifiers
REGION                  1..154
                        note = 41BB-Z endodomain fusion
source                  1..154
                        mol_type = protein
                        organism = synthetic construct
SEQUENCE: 27
KRGRKKLLYI FKQPFMRPVQ TTQEEDGCSC RFPEEEEGGC ELRVKFSRSA DAPAYQQGQN    60
QLYNELNLGR REEYDVLDKR RGRDPEMGGK PRRKNPQEGL YNELQKDKMA EAYSEIGMKG    120
ERRRGKGHDG LYQGLSTATK DTYDALHMQA LPPR                                154

SEQ ID NO: 28           moltype = AA   length = 149
```

-continued

```
FEATURE               Location/Qualifiers
REGION                1..149
                      note = OX40-Z endodomain fusion
source                1..149
                      mol_type = protein
                      organism = synthetic construct
SEQUENCE: 28
RRDQRLPPDA HKPPGGGSFR TPIQEEQADA HSTLAKIRVK FSRSADAPAY QQGQNQLYNE    60
LNLGRREEYD VLDKRRGRDP EMGGKPRRKN PQEGLYNELQ KDKMAEAYSE IGMKGERRRG   120
KGHDGLYQGL STATKDTYDA LHMQALPPR                                    149

SEQ ID NO: 29         moltype = AA   length = 151
FEATURE               Location/Qualifiers
REGION                1..151
                      note = CD28Z endodomain fusion
source                1..151
                      mol_type = protein
                      organism = synthetic construct
SEQUENCE: 29
KRSRLLHSDY MNMTPRRPGP TRKHYQPYAP PRDFAAYRSR VKFSRSADAP AYQQGQNQLY    60
NELNLGRREE YDVLDKRRGR DPEMGGKPRR KNPQEGLYNE LQKDKMAEAY SEIGMKGERR   120
RGKGHDGLYQ GLSTATKDTY DALHMQALPP R                                 151

SEQ ID NO: 30         moltype = AA   length = 187
FEATURE               Location/Qualifiers
REGION                1..187
                      note = CD28OXZ
source                1..187
                      mol_type = protein
                      organism = synthetic construct
SEQUENCE: 30
KRSRLLHSDY MNMTPRRPGP TRKHYQPYAP PRDFAAYRSR DQRLPPDAHK PPGGGSFRTP    60
IQEEQADAHS TLAKIRVKFS RSADAPAYQQ GQNQLYNELN LGRREEYDVL DKRRGRDPEM   120
GGKPRRKNPQ EGLYNELQKD KMAEAYSEIG MKGERRRGKG HDGLYQGLST ATKDTYDALH   180
MQALPPR                                                            187

SEQ ID NO: 31         moltype = AA   length = 20
FEATURE               Location/Qualifiers
REGION                1..20
                      note = signal peptide
source                1..20
                      mol_type = protein
                      organism = synthetic construct
SEQUENCE: 31
METDTLLLWV LLLWVPGSTG                                               20

SEQ ID NO: 32         moltype = AA   length = 234
FEATURE               Location/Qualifiers
REGION                1..234
                      note = spacer (hinge-CH2CH3 of human IgG1)
source                1..234
                      mol_type = protein
                      organism = synthetic construct
SEQUENCE: 32
AEPKSPDKTH TCPPCPAPPV AGPSVFLFPP KPKDTLMIAR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GKKD         234

SEQ ID NO: 33         moltype = AA   length = 46
FEATURE               Location/Qualifiers
REGION                1..46
                      note = spacer (human CD8 stalk)
source                1..46
                      mol_type = protein
                      organism = synthetic construct
SEQUENCE: 33
TTTPAPRPPT PAPTIASQPL SLRPEACRPA AGGAVHTRGL DFACDI                  46

SEQ ID NO: 34         moltype = AA   length = 20
FEATURE               Location/Qualifiers
REGION                1..20
                      note = spacer (human IgG1 hinge)
source                1..20
                      mol_type = protein
                      organism = synthetic construct
SEQUENCE: 34
AEPKSPDKTH TCPPCPKDPK                                               20
```

-continued

```
SEQ ID NO: 35              moltype = AA   length = 237
FEATURE                    Location/Qualifiers
REGION                     1..237
                           note = spacer (IgG1 Hinge-Fc)
source                     1..237
                           mol_type = protein
                           organism = synthetic construct
SEQUENCE: 35
AEPKSPDKTH TCPPCPAPEL LGGPSVFLFP PKPKDTLMIS RTPEVTCVVV DVSHEDPEVK  60
FNWYVDGVEV HNAKTKPREE QYNSTYRVVS VLTVLHQDWL NGKEYKCKVS NKALPAPIEK  120
TISKAKGQPR EPQVYTLPPS RDELTKNQVS LTCLVKGFYP SDIAVEWESN GQPENNYKTT  180
PPVLDSDGSF FLYSKLTVDK SRWQQGNVFS CSVMHEALHN HYTQKSLSLS PGKKDPK     237

SEQ ID NO: 36              moltype = AA   length = 236
FEATURE                    Location/Qualifiers
REGION                     1..236
                           note = spacer (IgG1 Hinge - Fc modified to remove Fc
                            receptor recognition motifs)
source                     1..236
                           mol_type = protein
                           organism = synthetic construct
SEQUENCE: 36
AEPKSPDKTH TCPPCPAPPV AGPSVFLFPP KPKDTLMIAR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GKKDPK      236

SEQ ID NO: 37              moltype = AA   length = 244
FEATURE                    Location/Qualifiers
REGION                     1..244
                           note = single-chain variable fragment (scFv),
                            scFv_fmc63_VH-VL
source                     1..244
                           mol_type = protein
                           organism = synthetic construct
SEQUENCE: 37
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY GGSYAMDYW GQGTSVTVSS   120
GGGGSGGGGS GGGGSDIQMT QTTSSLSASL GDRVTISCRA SQDISKYLNW YQQKPDGTVK  180
LLIYHTSRLH SGVPSRFSGS GSGTDYSLTI SNLEQEDIAT YFCQQGNTLP YTFGGGTKLE  240
ITKA                                                                 244

SEQ ID NO: 38              moltype = AA   length = 244
FEATURE                    Location/Qualifiers
REGION                     1..244
                           note = scFv, scFv_fmc63_VL-VH
source                     1..244
                           mol_type = protein
                           organism = synthetic construct
SEQUENCE: 38
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITKAG GGGSGGGGSG  120
GGGSEVKLQE SGPGLVAPSQ SLSVTCTVSG VSLPDYGVSW IRQPPRKGLE WLGVIWGSET  180
TYYNSALKSR LTIIKDNSKS QVFLKMNSLQ TDDTAIYYCA KHYYGGSYA MDYWGQGTSV   240
TVSS                                                                244

SEQ ID NO: 39              moltype = AA   length = 249
FEATURE                    Location/Qualifiers
REGION                     1..249
                           note = scFv, scFv_4g7_VH-VL
source                     1..249
                           mol_type = protein
                           organism = synthetic construct
SEQUENCE: 39
EVQLQQSGPE LIKPGASVKM SCKASGYTFT SYVMHWVKQK PGQGLEWIGY INPYNDGTKY  60
NEKFKGKATL TSDKSSSTAY MELSSLTSED SAVYYCARGT YYYGSRVFDY WGQGTTLTVS  120
SGGGGSGGGG SGGGGSDIVM TQAAPSIPVT PGESVSISCR SSKSLLNSNG NTYLYWFLQR  180
PGQSPQLLIY RMSNLASGVP DRFSGSGSGT AFTLRISRVE AEDVGVYYCM QHLEYPFTFG  240
AGTKLELKR                                                          249

SEQ ID NO: 40              moltype = AA   length = 250
FEATURE                    Location/Qualifiers
REGION                     1..250
                           note = scFv, scFv_4g7_VL-VH
source                     1..250
                           mol_type = protein
                           organism = synthetic construct
SEQUENCE: 40
DIVMTQAAPS IPVTPGESVS ISCRSSKSLL NSNGNTYLYW FLQRPGQSPQ LLIYRMSNLA  60
```

-continued

```
SGVPDRFSGS GSGTAFTLRI SRVEAEDVGV YYCMQHLEYP FTFGAGTKLE LKRSGGGGSG  120
GGGSGGGGSE VQLQQSGPEL IKPGASVKMS CKASGYTFTS YVMHWVKQKP GQGLEWIGYI  180
NPYNDGTKYN EKFKGKATLT SDKSSSTAYM ELSSLTSEDS AVYYCARGTY YYGSRVFDYW  240
GQGTTLTVSS                                                         250

SEQ ID NO: 41             moltype = AA  length = 242
FEATURE                   Location/Qualifiers
REGION                    1..242
                          note = scFv, scFv_CAT_VL-VH
source                    1..242
                          mol_type = protein
                          organism = synthetic construct
SEQUENCE: 41
QIVLTQSPAI MSASPGEKVT MTCSASSSVS YMHWYQQKSG TSPKRWIYDT SKLASGVPDR  60
FSGSGSGTSY FLTINNMEAE DAATYYCQQW NINPLTFGAG TKLELKRSGG GGSGGGGSGG  120
GGSQVQLQQS GPELVKPGAS VKISCKASGY AFSSSWMNWV KQRPGKGLEW IGRIYPGDED  180
TNYSGKFKDK ATLTADKSST TAYMQLSSLT SEDSAVYFCA RSLLYGDYLD YWGQGTTLTV  240
SS                                                                242

SEQ ID NO: 42             moltype = AA  length = 494
FEATURE                   Location/Qualifiers
REGION                    1..494
                          note = Fmc63_CAR
source                    1..494
                          mol_type = protein
                          organism = synthetic construct
SEQUENCE: 42
METDTLLLWV LLLWVPGSTG DIQMTQTTSS LSASLGDRVT ISCRASQDIS KYLNWYQQKP  60
DGTVKLLIYH TSRLHSGVPS RFSGSGSGTD YSLTISNLEQ EDIATYFCQQ GNTLPYTFGG  120
GTKLEITKAG GGGSGGGGSG GGGSGGGGSE VKLQESGPGL VAPSQSLSVT CTVSGVSLPD  180
YGVSWIRQPP RKGLEWLGVI WGSETTYYNS ALKSRLTIIK DNSKSQVFLK MNSLQTDDTA  240
IYYCAKHYYY GGSYAMDYWG QGTSVTVSSD PTTTPAPRPP TPAPTIASQP LSLRPEACRP  300
AAGGAVHTRG LDFACDIYIW APLAGTCGVL LLSLVITLYC KRGRKKLLYI FKQPFMRPVQ  360
TTQEEDGCSC RFPEEEEGGC ELRVKFSRSA DAPAYQQGQN QLYNELNLGR REEYDVLDKR  420
RGRDPEMGGK PRRKNPQEGL YNELQKDKMA EAYSEIGMKG ERRRGKGHDG LYQGLSTATK  480
DTYDALHMQA LPPR                                                    494

SEQ ID NO: 43             moltype = AA  length = 18
FEATURE                   Location/Qualifiers
REGION                    1..18
                          note = Linker
source                    1..18
                          mol_type = protein
                          organism = synthetic construct
SEQUENCE: 43
SGGGGSSGGG GSSGGGGS                                                18
```

CHIMERIC ANTIGEN RECEPTOR (CAR) COMPRISING A CD19-BINDING DOMAIN

CROSS-REFERENCE TO RELATED APPLICATIONS

This application is a Continuation of U.S. patent application Ser. No. 16/573,854, filed on Sep. 17, 2019; which is a Continuation of U.S. patent application Ser. No. 15/555, 508, national stage filed on Sep. 3, 2017, which is a U.S. National Phase of International Patent Application No. PCT/GB2016/050574, filed on Mar. 4, 2016; which claims priority from Application 1503742.7, filed on Mar. 5, 2015 in the United Kingdom.

INCORPORATION BY REFERENCE OF ELECTRONIC SEQUENCE LISTING

This application contains a Sequence Listing which has been submitted electronically in .xml format and is hereby incorporated by reference in its entirety. This .xml copy was created on Dec. 7, 2022, is named 52309B_Seqlisting.xml, and is 61,390 bytes in size.

FIELD OF THE INVENTION

The present invention relates to a chimeric antigen receptor (CAR) which binds the B-lymphocyte antigen CD19 (Cluster of Differentiation 19). T cells expressing such a CAR are useful in the treatment of cancerous diseases such as B-cell leukemias and lymphomas.

BACKGROUND TO THE INVENTION

Chimeric Antigen Receptors

Traditionally, antigen-specific T-cells have been generated by selective expansion of peripheral blood T-cells natively specific for the target antigen. However, it is difficult and quite often impossible to select and expand large numbers of T-cells specific for most cancer antigens. Gene-therapy with integrating vectors affords us a solution to this problem: transgenic expression of Chimeric Antigen Receptor (CAR) allows large numbers of T-cells specific to any surface antigen to be easily generated by ex vivo viral vector transduction of a bulk population of peripheral blood T-cells.

The most common forms of these molecules are fusions of single-chain variable fragments (scFv) derived from monoclonal antibodies which recognise a target antigen, fused via a spacer and a transmembrane domain to a signalling endodomain. Such molecules result in activation of the T-cell in response to recognition by the scFv of its cognate target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers. To-date however, the main clinical exploration and potential application of CAR therapy is as treatment for B-cell malignancies.

CARs Directed Against CD19

CD19 is a B-cell antigen which is expressed very early in B-cell differentiation and is only lost at terminal B-cell differentiation into plasma cells. Hence, CD19 is expressed on all B-cell malignancies apart from multiple myeloma. It is not expressed on other haematopoietic populations or non-haematopoietic cells and therefore targeting this antigen should not lead to toxicity to the bone marrow or non-haematopoietic organs. Loss of the normal B-cell compartment is considered an acceptable toxicity when treating lymphoid malignancies, because although effective CD19 CAR T cell therapy will result in B cell aplasia, the consequent hypogammaglobulinaemia can be treated with pooled immunoglobulin.

CD19 is therefore an attractive CAR target. To date, the main clinical focus of the CAR field has been studies targeting CD19 on refractory B-cell cancers, as summarised in Table 1.

Different designs of CARs have been tested against CD19 in different centres, as outlined in Table 1:

TABLE 1

| Summary of CAR experience targeting CD19 | | | |
| --- | --- | --- | --- |
| Centre | Binder | Endodomain | Comment |
| University College London | Fmc63 | CD3-Zeta | Low-level brief persistence |
| Memorial Sloane Kettering | SJ25C1 | CD28-Zeta | Short-term persistence |
| NCI/KITE | Fmc63 | CD28-Zeta | Long-term low-level persistence |
| Baylor, Centre for Cell and Gene Therapy | Fmc63 | CD3-Zeta/CD28-Zeta | Short-term low-level persistence |
| UPENN/Novartis | Fmc63 | 41BB-Zeta | Long-term high-level persistence |

Most of the studies have tested CD19 CARs based on a scFv derived from the hybridoma fmc63. The most promising have been in the treatment of Acute Lymphoblastic Leukaemia (ALL).

Clinical Experience with CARs Against CD19

CD19 directed CAR therapy appears most effective in ALL. The first studies in ALL were published in Spring 2013, by groups from Memorial Sloane Kettering (Brentjens, et al. (2013) Leukemia. Sci. Transl. Med. 5, 177ra38) and the University of Pennsylvania. An update report of the latter study has recently been made (Maude et al. (2014) N. Engl. J. Med. 371, 1507-1517). Here, 25 patients under the age of 25 years and 5 over this age were treated. 90% achieved a complete response at one month, 22 of 28 evaluable cases achieved an MRD negative status and the 6 month event free survival rate was 67%. 15 patients received no further therapy after the study.

Brentjens et al., (as above) in the adult setting, treated 5 ALL patients (2 with refractory relapse, 2 with MRD positive disease and 1 who was MRD negative) with autologous T cells retrovirally transduced to express a CD19 CAR incorporating an scFv derived from the SJ25C1 hybridoma and a CD28 co-stimulatory domain. All of these achieved a deep molecular remission, enabling 4 of these patients to receive an allogeneic SCT. This precluded assessment of the durability of responses but CAR T cells were only detectable in the blood or bone marrow for 3-8 weeks after infusion. The patient who was not transplanted relapsed at 90 days with CD19+ disease. Subsequently, Davila et al. ((2014). Sci. Transl. Med. 6, 224ra25) have updated this cohort. 14 of 16 adult patients had detectable disease at the point of CAR T cell infusion, despite salvage chemotherapy and cyclophosphamide conditioning. 14 of 16 achieved a complete remission with or without count recovery including 7 of 9 patients with morphologic evidence of residual disease detectable after salvage chemotherapy. 12 of 16 patients achieved MRD negativity and this allowed 7 to undergo allogeneic transplantation by the time of publication.

Responses were durable in some patients with 4 of 8 non-transplanted patients continuing in morphological remission at up to 24 months follow-up although the survival curves for this cohort are not yet stable.

A recently published study in a cohort of paediatric and young adult patients predominantly with ALL provides the first intention-to-treat analysis of its outcomes. This may help remove the bias inherent in excluding patients who do not receive the anticipated dose of CAR T cells (Lee et al. (2014) Lancet. doi:10.1016/50140-6736(14)61403-3). 21 patients were treated with a CD28 domain-containing second generation CAR. All but 2 patients received the anticipated T cell dose, highlighting the feasibility of delivering this treatment to those with refractory or multiply-relapsed ALL. This study shows the following efficacy: 67% achieving a complete remission and 60% of those with ALL achieving MRD negative status.

Immune Toxicity of CD19 CAR Therapy

Cytokine release syndrome (CRS) encompasses a range of inflammatory symptoms ranging from mild to multi-organ failure with hypotension and respiratory failure. Some degree of CRS occurs commonly in patients treated with CD19 CAR T cells. Approximately 30% (21/73) patients treated in recent cohorts showed some degree of CRS (Davilia et al (2014) as above; Lee et al (2014) as above; Kochenderfer (2014) J. Clin. Oncol. Off. J. Am. Soc. Clin. Oncol. doi:10.1200/JCO.2014.56.2025). CRS has also been seen in patients treated with blinatumomab, a bi-specific recombinant single-chain antibody recognising both CD19 and CD3. CRS typically occurs 5-21 days after CAR T cell infusion.

CRS can be life threatening and requires treatment in an intensive care setting. CRS is associated with elevated serum cytokine levels. The cytokines most significantly elevated are IL-6, IL-10 and interferon gamma (IFNγ). Clinical manifestations of severe CRS (fever, hepatosplenomegaly, coagulopathy and hyperferritinaemia) resemble macrophage activation syndrome (MAS) found for instance in patients with congenital defects in T-cells. This suggests that common immunopathological processes are involved. At present it is not clear which cell type (CAR T cells, dying tumour cells, or locally-activated macrophages) are responsible for production of the key cytokines, particularly IL-6. However, a key initiating factor in MAS is release of copious Interferon-gamma (Lopez-Alvarez et al. (2009). Clin. Vaccine Immunol. CVI 16, 142-145).

Neurotoxicity

A number of patients in CD19 CAR studies across institutions have developed transient neurotoxicity with a spectrum of severity from aphasia to obtundation, delirium and seizures (Davilia et al (2014) as above). This appears to be restricted to patients with ALL and a similar syndrome has been documented after blinatumomab therapy. Brain imaging appears normal. Neurotoxicity may reflect high levels of systemic cytokines crossing the blood-brain barrier.

Persistence, Relapse and T-Cell Exhaustion

Durable responses appeared to correlate with higher peak levels of circulating CAR transduced T cells, as well as with the duration of B cell aplasia. With exception of patients relapsing with CD19− disease, relapse was generally associated with loss of circulating CAR T cells and recovery of normal B cells.

T cell exhaustion is a state of T cell dysfunction that arises during many chronic infections and cancer. It is defined by poor effector function, sustained expression of inhibitory receptors and a transcriptional state distinct from that of functional effector or memory T cells. Exhaustion prevents optimal control of infection and tumors. Recently, a clearer picture of the functional and phenotypic profile of exhausted T cells has emerged with expression of inhibitory receptor programmed death 1 (PD-1; also known as PDCD1), a negative regulator of activated T cells, being a key feature (Day et al. (2006) Nature 443, 350-354).

Responses in CD19 CAR studies suggest that persistence of T-cells for a protracted period at high levels seems to be important in effecting durable responses. A CD19 CAR which reduces T-cell exhaustion may result in improved clinical responses.

There is thus a need for an alternative CAR directed against CD19 which is not associated with the above disadvantages.

DESCRIPTION OF THE FIGURES

FIG. 1. Annotated and numbered (a) CAT19 VH sequences; (b) CAT19 VL

Sequences of the VH and VL are numbered using Chothia numbering. The framework and CDR regions are shown. Insertions are also shown.

Figure 2:
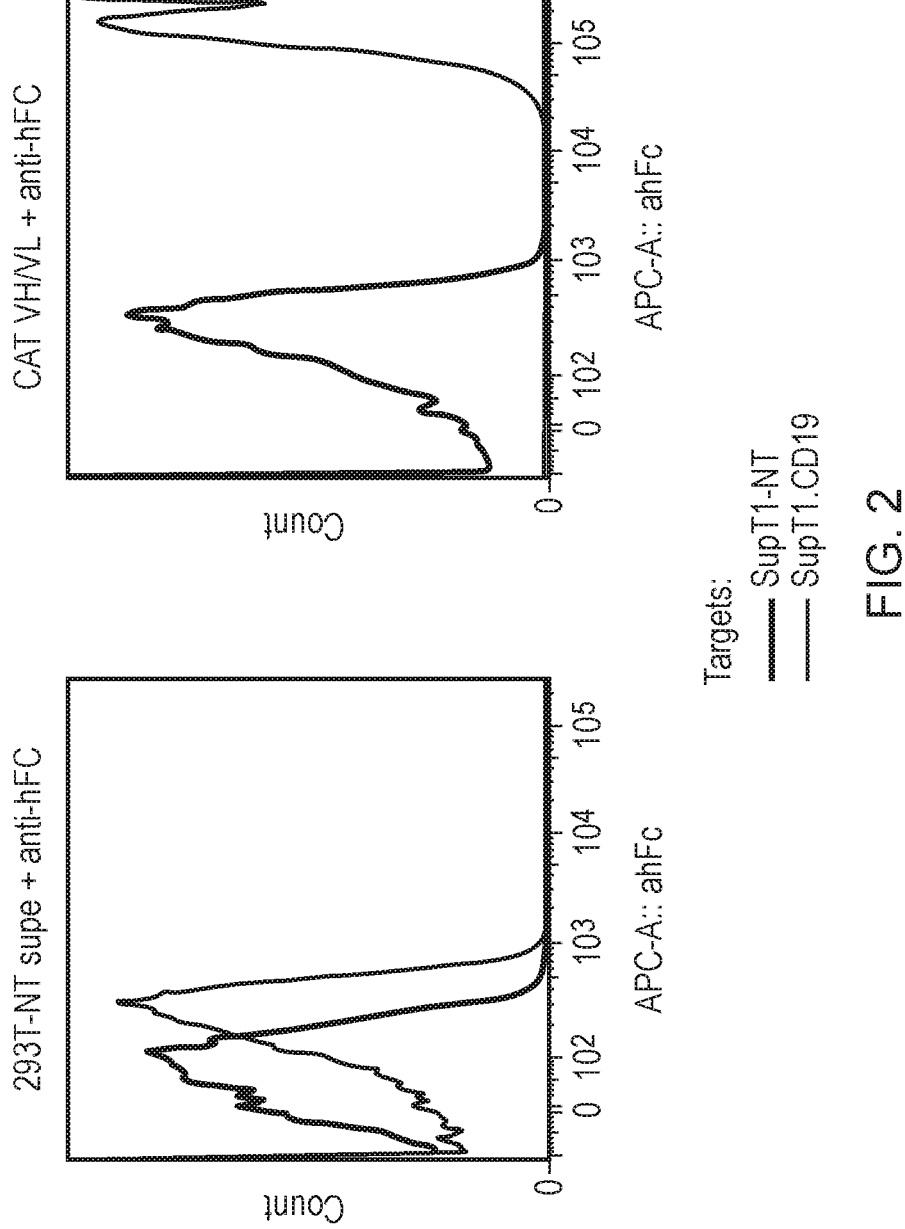

FIG. 2. Staining of CD19 positive cells with recombinant CAT19

SupT1 cells do not normally express CD19 but were engineered to do so in this study. CAT19 VH and VL sequences were cloned into mouse IgG2a heavy chain format and mouse kappa light chain format, both in mammalian expression plasmids. 293T cells were transfected simultaneously with both heavy and light chain and the resultant antibody purified with protein A. SupT1 cells and SupT1.CD19 cells were stained with this recombinant antibody (or plain 293T supernatant) and further stained with a fluorescently conjugated anti-mouse secondary. Binding of recombinant CAT19 antibody could readily be detected by flow-cytometry.

Figure 3:
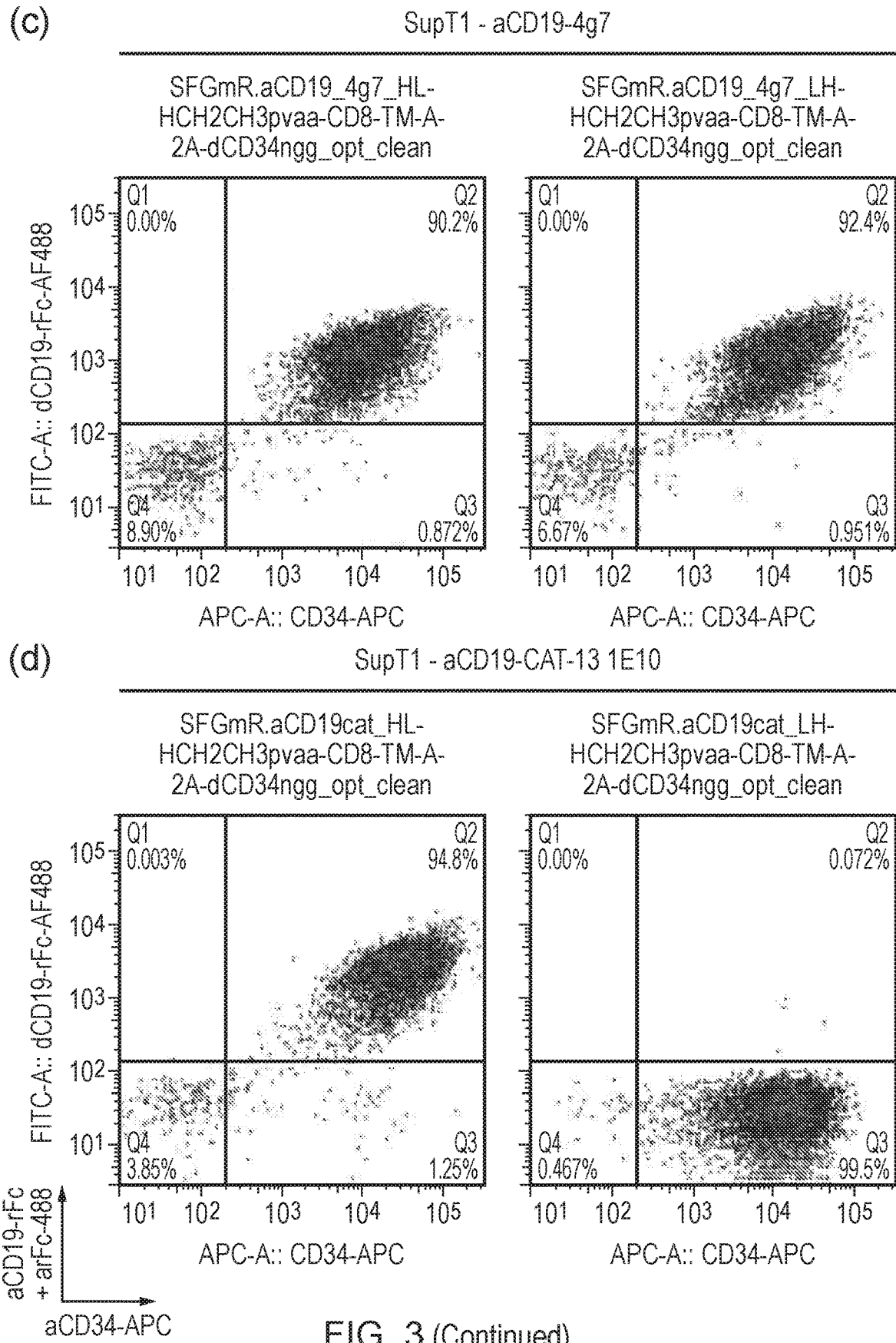

FIG. 3. Staining of CD19 positive cells with CAT19 scFv

The VH and VL of CAT19 were cloned such that they form a scFv whereby the VH and VL are separated by a $(SGGGGS)_3$ linker. Two scFvs were generated with the CAT scFv in both VH-VL and VL-VH orientations. In addition, scFvs were generated, also in either orientation, from the anti-CD19 antibodies fmc63 and 4g7. (a) scFv display format: this is a retroviral vector whereby the scFv is cloned onto a human IgG1 Fc spacer which has the CD8 transmembrane domain and the first 12 residues of the CD8 endodomain. This in turn is in frame with the FMD-2A peptide TaV and truncated human CD34. In this way, the scFv is displayed on the surface of a cell, and the transgene expression can be controlled for by detecting CD34 separately. SupT1 cells were generated which express either of the 6 different scFv formats and these cells were stained with recombinant human truncated CD19—mouse IgG2a Fc fusion and anti-CD34; (b) Staining with fmc63 VH-VL and VL-VH format; (c) Staining with 4g7 VH-VL and VL-VH format; and (d) Staining with CAT19 VH-VL and VL-VH format. Surprisingly, the CAT19 VH-VL scFv bound well, while the VL-VH scFv gave significantly less detectable binding.

Figure 4:
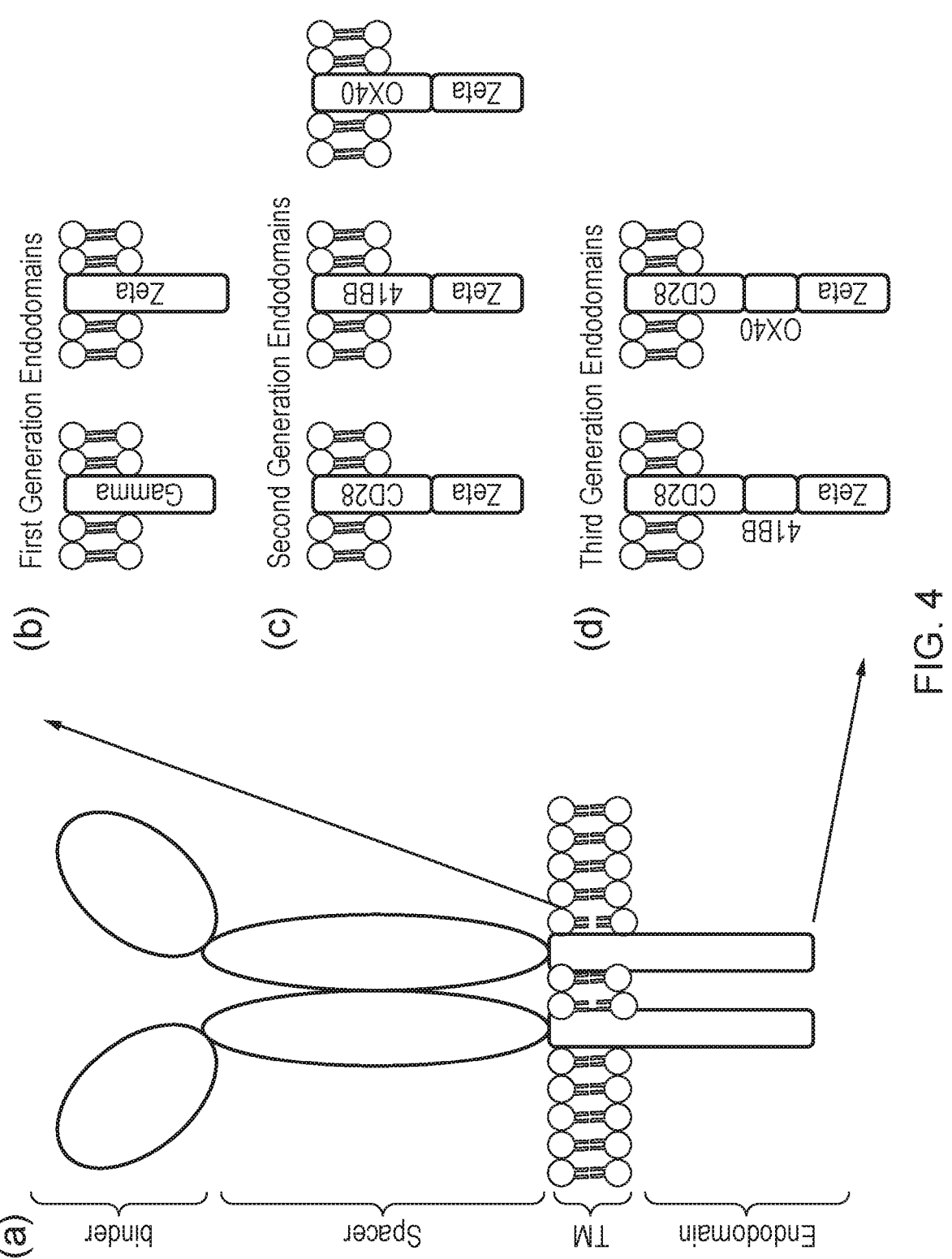
Figure 4:
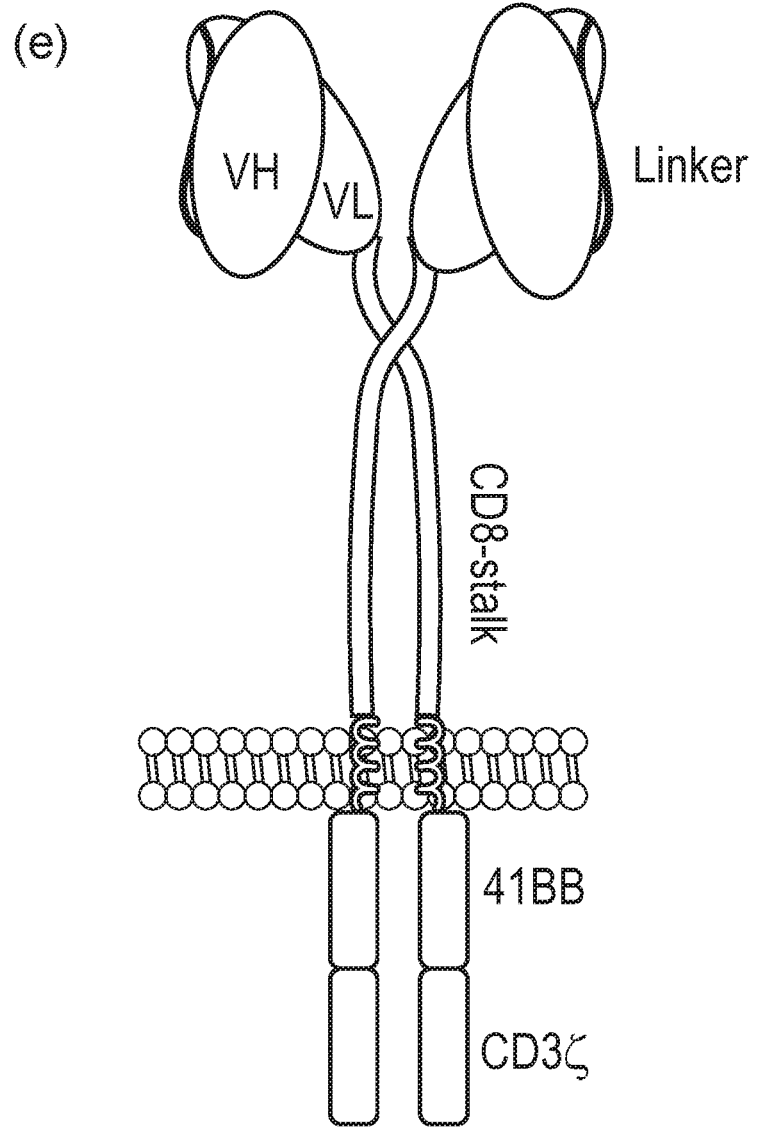

FIG. 4. Different generations of CARs and initial CARs tested (a) A typical CAR format comprising of an antigen binding domain (which most usually is a scFv), a spacer domain, a transmembrane domain and one or several signalling domains. (b) First generation CARs transmit an activation signal; their endodomain is derived from either the FcGamma receptor endodomain or the CD3 Zeta endodomain; (c) Second generation receptors transmit two signals: their endodomains comprise a co-stimulatory domain connected to the endodomain of CD3-Zeta. The co-stimulatory domain is usually either the endodomain of CD28, the endodomain of OX40 or the endodomain of 41BB. (d) Third generation receptors transmit three signals: their endodomains comprise a fusion of the CD28 endodomain with the 41BB endodomain and with the CD3-Zeta endodomain, or the CD28 endodomain with the OX40 endodomain and with the CD3-Zeta endodomain. (e) The CAT19 based CAR initially tested which comprises a scFv in the VH-VL orientation, a CD8 stalk spacer and $2^{nd}$ generation endodomain comprising of 41BB-Zeta (Campana CAR format).

Figure 5:
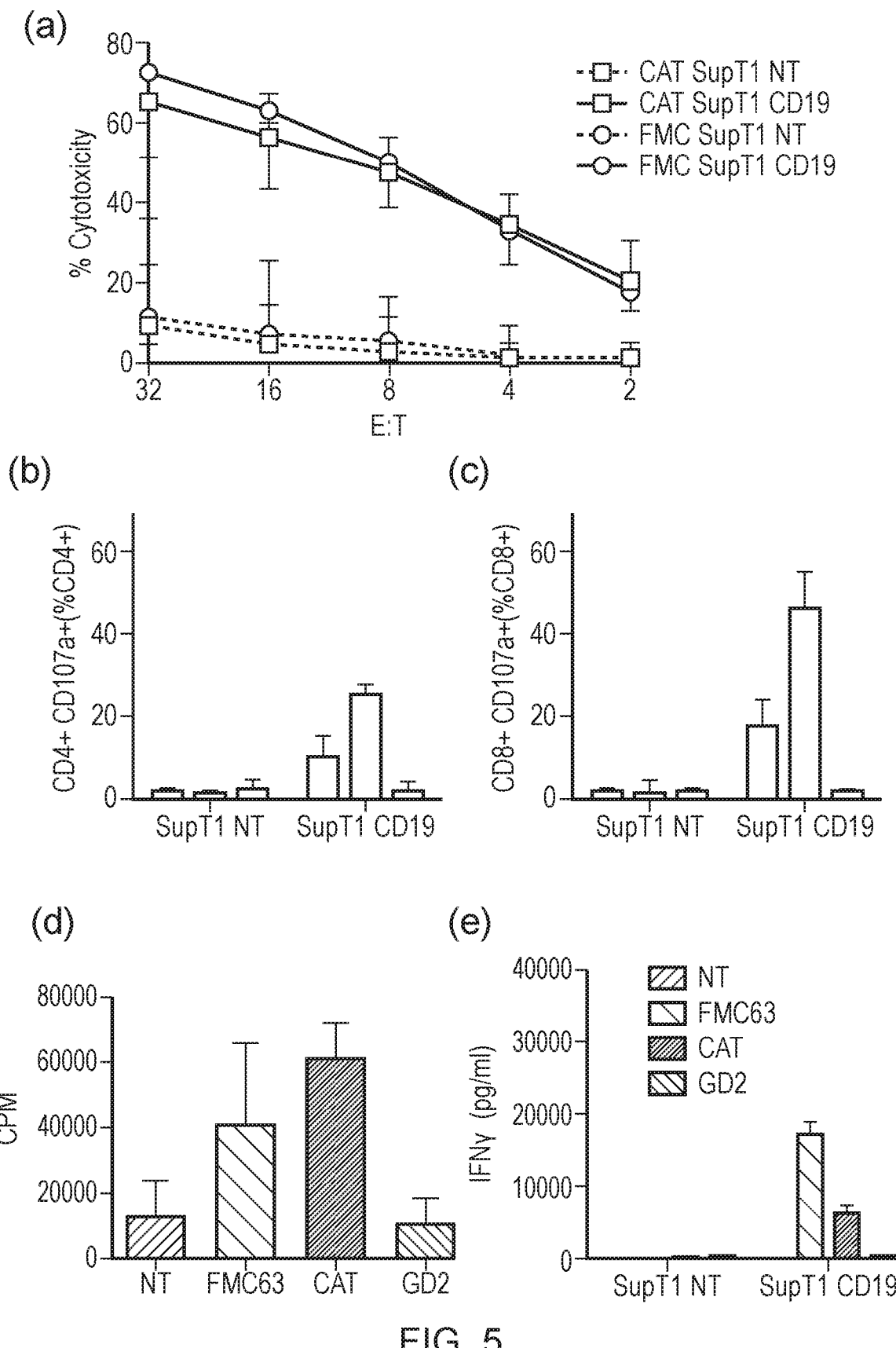

FIG. 5. In vitro comparison of CAT19 CAR function against fmc36 CAR

Primary human T-cells from 5 different donors were transduced with lentiviral vectors coding for CAT19 CAR in Campana format, or the Campana CAR itself. These T-cells were then used in various assays. (a) Chromium release assay was performed against SupT1 cells. These cells are CD19 negative. Neither CAR T-cells responded against this cell line (dotted lines). Chromium release assay was performed against SupT1.CD9. Both CARs performed equally against this cell line (unbroken lines). Next a degranulation assay was performed using either NT T-cells, fmc63 CAR T-cells, or CAT19 CAR T-cells against either SupT1 or SupT1.CD19. (b) data gated on CD4+ T-cells, and (c) CD8+ T-cells is shown. Degranulation was increased with CAR19 CAR T-cells. (d) Proliferation was estimated using tritiated thymidilation incorporation. NT, fmc63 CAR T-cells, CAT19 CAR T-cells were tested against SupT1. CD19. In this experiment, an irrelevant CAR targeting GD2 was also tested. There was a trend to increased proliferation with CAR19 CAR T-cells. (e) Interferon-gamma release from either NT T-cells, fmc63 CAR T-cells, CAT19 CAR T-cells or GD2 CAR T-cells 24 hours after challenge against SupT1 or SupT1.CD19 cells. CAT19 CAR T-cells produced significantly less IF-G than fmc63 CAR T-cells when challenged with CD19+ targets.

Figure 6:
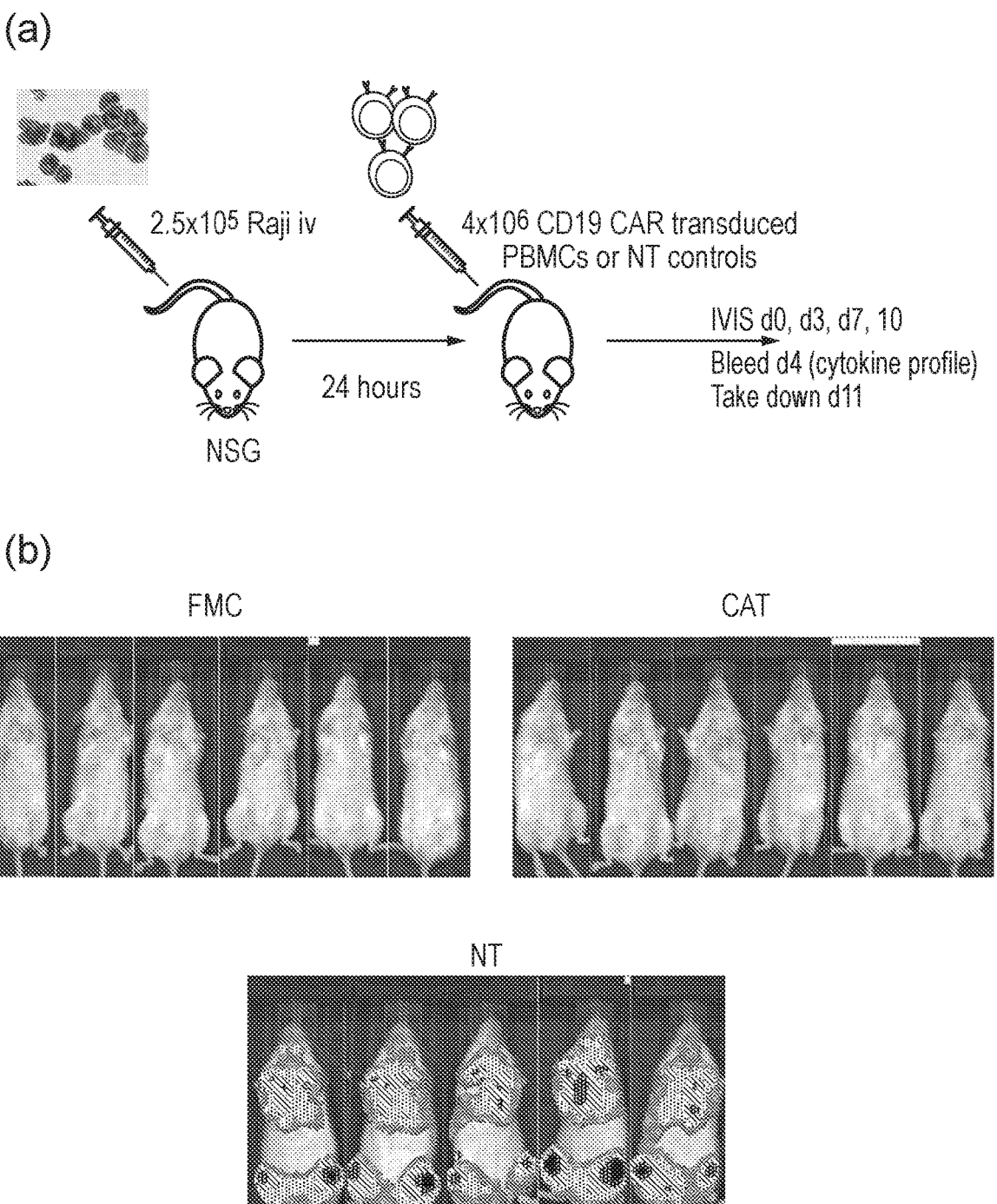

FIG. 6. In vivo model of CAT19 efficacy.

(a) Outline of experimental set-up for in vivo model. NSG mice were injected with 2.5×10^5 Raji.FLuc cells via tail vein injection. 24 hours later 4×10^6 of either NT primary human T-cells, or T-cells transduced with fmc63 CAR, or T-cells transduced with CAT19 CAR were administered via tail-vein. Tumour response was measured sequentially by bioluminescence imaging. Tail-vein blood was sampled at day 4 for engraftment and serum cytokine. The animals were culled at day 11 and tissues studied for persistence of CAR T-cells and tumour burden. (b) Bioluminescence imaging of the different mouse cohorts at day 10. Extensive disease is seen in the pelvis, spine, ribs, skull and spleen of mice treated with NT T-cells, while minimal signal is evident in mice who received either CAT19 CAR T-cells, or fmc63 CAR T-cells. (c) Quantitative bioluminescent signal averaged from different mouse cohorts over time. Y-axis is a log-scale; A clear difference is seen between signal accumulation in mice who received NT T-cells, and mice who received CAR T-cells. No difference in signal accumulation is seen in mice who received fmc63 CAR T-cells or CAT19 CAR T-cells. (d) Flow-cytometric determined tumour burden in bone-marrow from mice at the end of the experiment. Practically no Raji cells could be detected in marrow of mice who received either fmc63 or CAT19 CAR T-cells.

Figure 7:
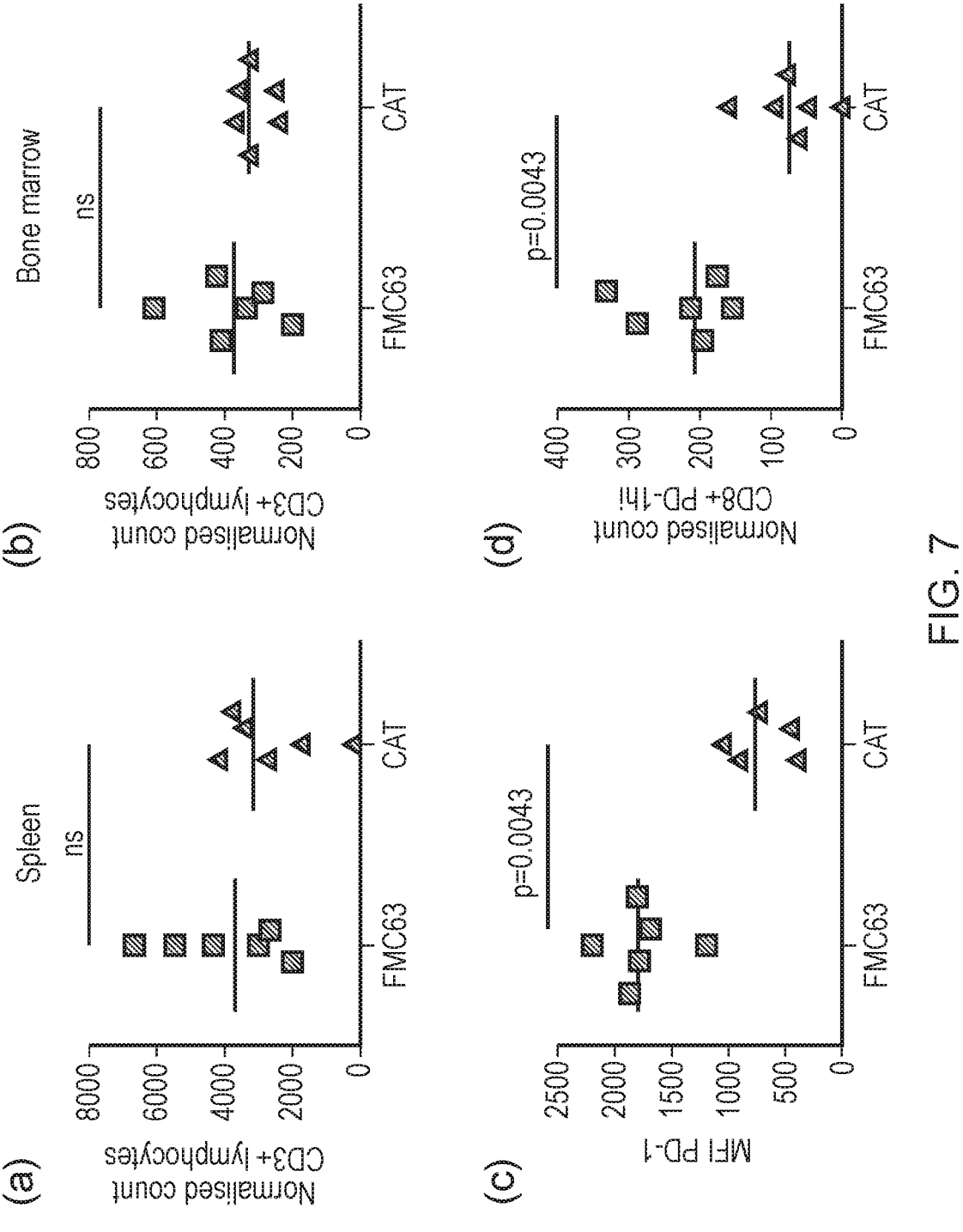

FIG. 7. Characterization of in vivo persisting CAR T-cells (a) Absolute numbers of CAR T-cells in spleens of mice from animals treated with fmc63 CAR T-cells or CAT19 CAR T-cells in the model outlined above. This shows the same numbers are present in both; (b) Absolute numbers of CAR T-cells in bone-marrow of mice treated with fmc63 CAR T-cells or CAT19 CAR T-cells. This shows the same numbers of cells are present in both; (c) Absolute numbers of PD1-expressing CAR T-cells in spleen and (d) bone-marrow of mice treated with either fmc63 CAR T-cells or CAT19 CAR T-cells. Fewer of the CAT19 T-cells are PD1+ in both compartments.

SUMMARY OF ASPECTS OF THE INVENTION

The present inventors have developed a new CD19-specific CAR with CDRs that have not previously been described. It has equivalent potency to the fmc63-based CAR used in the UPENN studies, but results in reduced toxicity and reduced T-cell exhaustion.

Thus, in a first aspect the present invention provides a chimeric antigen receptor (CAR) comprising a CD19-binding domain which comprises a) a heavy chain variable region (VH) having complementarity determining regions (CDRs) with the following sequences:

```
CDR1
                          (SEQ ID No. 1)
GYAFSSS;

CDR2
                          (SEQ ID No. 2)
YPGDED

CDR3
                          (SEQ ID No. 3)
SLLYGDYLDY;
``` and
  b) a light chain variable region (VL) having CDRs with
     the following sequences:

```
CDR1
                          (SEQ ID No. 4)
SASSSVSYMH;

CDR2
                          (SEQ ID No. 5)
DTSKLAS

CDR3
                          (SEQ ID No. 6)
QQWNINPLT.
```

The CD19 binding domain may comprise a VH domain having the sequence shown as SEQ ID No. 7 and/or or a VL domain having the sequence shown as SEQ ID No 8 or a variant thereof having at least 95% sequence identity.

The CD19 binding domain may comprise an scFv in the orientation VH-VL.

The CD19 binding domain may comprise the sequence shown as SEQ ID No 9 or a variant thereof having at least 90% sequence identity.

The CD19 binding domain may comprise the 6 CDRs defined in claim 1 grafted on to a human antibody framework.

The CD19-binding domain and the transmembrane domain may be connected by a spacer, which may comprise one of the following: a human an IgG1 Fc domain; an IgG1 hinge; or a CD8 stalk. The spacer may comprise a CD8 stalk.

The CAR may comprise or associate with an intracellular T cell signalling domain.

The intracellular T cell signalling domain may comprise one or more of the following endodomains: CD28 endodomain; 41BB endodomain, OX40 endodomain and the CD3-Zeta endodomain.

In particular the CAR may comprise a CD8 stalk spacer and an intracellular T-cell signalling domain which comprises the 41BB endodomain and the CD3-Zeta endodomain.

In particular the CAR may comprise a CD8 stalk spacer and an intracellular T-cell signalling domain which comprises the OX40 endodomain and the CD3-Zeta endodomain.

In an alternative embodiment, the intracellular T cell signalling domain may comprise all of the following endodomains: CD28 endodomain; OX40 and CD3-Zeta endodomain.

The CAR may comprise the sequence shown as any of SEQ ID No. 10 to 15 or a variant thereof which has at least 80% sequence identity but retains the capacity to i) bind CD19 and ii) induce T cell signalling. The CAR may have advantageous properties compared to the fmc63-based CAR used in the UPENN studies. For example, the CAR, when expressed by a T-cell and used to target a CD19 expressing cell, may cause lower $IFN\gamma$ release by the CD19-expressing target cell than that caused by a T-cell expressing a CAR comprising a CD19-binding domain which comprises: a) a heavy chain variable region (VH) having complementarity determining regions (CDRs) with the following sequences: CDR1—GVSLPDY (SEQ ID No. 16); CDR2—WGSET (SEQ ID No. 17); CDR3—HYYYGGSYAMDY (SEQ ID No. 18); and b) a light chain variable region (VL) having CDRs with the following sequences:CDR1—RASQDIS-KYLN (SEQ ID No. 19); CDR2—HTSRLHS (SEQ ID No. 20) CDR3—QQGNTLPYT (SEQ ID No. 21). The CDRs may be grafted on to a human or humanised framework.

In a second aspect, the present invention provides a nucleic acid sequence which encodes a CAR according to the first aspect of the invention.

In a third aspect, there is provided a vector which comprises a nucleic acid sequence according to the second aspect of the invention.

In a third aspect there is provided a cell which comprises a CAR according to the first aspect of the invention.

The cell may be a cytolytic immune cell, such as a T cell or a natural killer (NK) cell.

In a fourth aspect there is provided a cell composition which comprises a plurality of cells according to the third aspect of the invention.

In a fifth aspect, there is provided a method for making a cell according to the third aspect of the invention, which comprises the step of transducing or transfecting a cell with a vector according to the third aspect of the invention.

In a sixth aspect there is provided a method for making a cell composition according to the fourth aspect of the invention which comprises the step of transducing or transfecting a sample of cells from a subject ex vivo with a vector according to the third aspect of the invention.

The sample of cells may, for example, be a blood sample or a derivative thereof, such as a peripheral blood mononuclear cell (PBMC) sample.

In a seventh aspect, there is provided a pharmaceutical composition which comprises a cell according to the first aspect of the invention, or a cell composition according to the fourth aspect of the invention, together with a pharmaceutically acceptable carrier, diluent or excipient.

In an eighth aspect, there is provided a method for treating cancer which comprises the step of administering a cell according to the first aspect of the invention, a cell composition according to the fourth aspect of the invention or a pharmaceutical composition according to the seventh aspect of the invention to a subject.

The method may comprise the step of transducing or transfecting cells from the subject ex vivo with a vector according to the third aspect of the invention, then administering the, or some of the, transfected cells back to the subject.

There is also provided a pharmaceutical composition according to the seventh aspect of the invention for use in treating cancer.

There is also provided the use of a cell according to the third aspect of the invention in the manufacture of a pharmaceutical composition for treating cancer.

The cancer may, for example, be a B cell malignancy.

DETAILED DESCRIPTION

Chimeric Antigen Receptors (CARs)

Chimeric antigen receptors (CARs), also known as chimeric T cell receptors, artificial T cell receptors and chimeric immunoreceptors, are engineered receptors, which graft an arbitrary specificity onto an immune effector cell. In a classical CAR, the specificity of a monoclonal antibody is grafted on to a T cell. CAR-encoding nucleic acids may be transferred to T cells using, for example, retroviral vectors. In this way, a large number of cancer-specific T cells can be generated for adoptive cell transfer. Phase I clinical studies of this approach show efficacy.

The target-antigen binding domain of a CAR is commonly fused via a spacer and transmembrane domain to an endodomain. The endodomain may comprise or associate with an intracellular T-cell signalling domain. When the CAR binds the target-antigen, this results in the transmission of an activating signal to the T-cell it is expressed on.

The CAR of the present invention comprises a CD19 binding domain which is based on a mouse anti-CD19 monoclonal antibody.

The CAR of the present invention comprises a CD19-binding domain which comprises a) a heavy chain variable region (VH) having complementarity determining regions (CDRs) with the following sequences:

```
        CDR1
                            (SEQ ID No. 1)
        GYAFSSS;

CDR2
                            (SEQ ID No. 2)
        YPGDED

CDR3
                            (SEQ ID No. 3)
        SLLYGDYLDY;
``` and b) a light chain variable region (VL) having CDRs with the following sequences:

```
        CDR1
                            (SEQ ID No. 4)
        SASSSVSYMH;
```

-continued
```
CDR2
                              (SEQ ID No. 5)
DTSKLAS

CDR3
                              (SEQ ID No. 6)
QQWNINPLT.
```

It may be possible to introduce one or more mutations (substitutions, additions or deletions) into each CDR without negatively affecting CD19-binding activity. Each CDR may, for example, have one, two or three amino acid mutations.

The CDRs may be in the format of a single-chain variable fragment (scFv), which is a fusion protein of the heavy variable region (VH) and light chain variable region (VL) of an antibody, connected with a short linker peptide of ten to about 25 amino acids. The scFv may be in the orientation VH-VL, i.e. the VH is at the amino-terminus of the CAR molecule and the VL domain is linked to the spacer and, in turn the transmembrane domain and endodomain.

The CDRs may be grafted on to the framework of a human antibody or scFv. For example, the CAR of the present invention may comprise a CD19-binding domain consisting or comprising one of the following sequences The CAR of the present invention may comprise the following VH sequence:

```
VH sequence from murine monoclonal antibody
                              SEQ ID No. 7
QVQLQQSGPELVKPGASVKISCKASGYAFSSSWMN

WVKQRPGKGLEWIGRIYPGDEDTNYSGKFKDKATL

TADKSSTTAYMQLSSLTSEDSAVYFCARSLLYGDY

LDYWGQGTTLTVSS
```

The CAR of the present invention may comprise the following VL sequence:

```
VL sequence from murine monoclonal antibody
                              SEQ ID No. 8
QIVLTQSPAIMSASPGEKVTMTCSASSSVSYMHWY

QQKSGTSPKRWIYDTSKLASGVPDRFSGSGSGTSY

FLTINNMEAEDAATYYCQQWNINPLTFGAGTKLEL

KR
```

The CAR of the invention may comprise the following scFv sequence:

```
VH-VL scFv sequence from murine
monoclonal antibody
                              SEQ ID No 9
QVQLQQSGPELVKPGASVKISCKASGYAFSSSWMN

WVKQRPGKGLEWIGRIYPGDEDTNYSGKFKDKATL

TADKSSTTAYMQLSSLTSEDSAVYFCARSLLYGDY

LDYWGQGTTLTVSSGGGGSGGGGSGGGGSQIVLTQ

SPAIMSASPGEKVTMTCSASSSVSYMHWYQQKSGT

SPKRWIYDTSKLASGVPDRFSGSGSGTSYFLTINN

MEAEDAATYYCQQWNINPLTFGAGTKLELKR
```

The CAR may consist of or comprise one of the following sequences:
CAT19 CAR using "Campana" architecture (see Examples)

```
                              SEQ ID No. 10
MGTSLLCWMALCLLGADHADAQVQLQQSGPELVKP

GASVKISCKASGYAFSSSWMNWVKQRPGKGLEWIG

RIYPGDEDTNYSGKFKDKATLTADKSSTTAYMQLS

SLTSEDSAVYFCARSLLYGDYLDYWGQGTTLTVSS

GGGGSGGGGSGGGGSQIVLTQSPAIMSASPGEKVT

MTCSASSSVSYMHWYQQKSGTSPKRWIYDTSKLAS

GVPDRFSGSGSGTSYFLTINNMEAEDAATYYCQQW

NINPLTFGAGTKLELKRSDPTTTPAPRPPTPAPTI

ASQPLSLRPEACRPAAGGAVHTRGLDFACDIYIWA

PLAGTCGVLLLSLVITLYCKRGRKKLLYIFKQPFM

RPVQTTQEEDGCSCRFPEEEEGGCELRVKFSRSAD

APAYQQGQNQLYNELNLGRREEYDVLDKRRGRDPE

MGGKPRRKNPQEGLYNELQKDKMAEAYSEIGMKGE

RRRGKGHDGLYQGLSTATKDTYDALHMQALPPR
```

CAT19 CAR with an OX40-Zeta endodomain
```
                              SEQ ID No. 11
MGTSLLCWMALCLLGADHADAQVQLQQSGPELVKP

GASVKISCKASGYAFSSSWMNWVKQRPGKGLEWIG

RIYPGDEDTNYSGKFKDKATLTADKSSTTAYMQLS

SLTSEDSAVYFCARSLLYGDYLDYWGQGTTLTVSS

GGGGSGGGGSGGGGSQIVLTQSPAIMSASPGEKVT

MTCSASSSVSYMHWYQQKSGTSPKRWIYDTSKLAS

GVPDRFSGSGSGTSYFLTINNMEAEDAATYYCQQW

NINPLTFGAGTKLELKRSDPTTTPAPRPPTPAPTI

ASQPLSLRPEACRPAAGGAVHTRGLDFACDIYIWA

PLAGTCGVLLLSLVITLYCRRDQRLPPDAHKPPGG

GSFRTPIQEEQADAHSTLAKIRVKFSRSADAPAYQ

QGQNQLYNELNLGRREEYDVLDKRRGRDPEMGGKP

RRKNPQEGLYNELQKDKMAEAYSEIGMKGERRRGK

GHDGLYQGLSTATKDTYDALHMQALPPR
```

CAT19 CAR with a CD28-Zeta endodomain
```
                              SEQ ID No. 12
MGTSLLCWMALCLLGADHADAQVQLQQSGPELVKP

GASVKISCKASGYAFSSSWMNWVKQRPGKGLEWIG

RIYPGDEDTNYSGKFKDKATLTADKSSTTAYMQLS

SLTSEDSAVYFCARSLLYGDYLDYWGQGTTLTVSS

GGGGSGGGGSGGGGSQIVLTQSPAIMSASPGEKVT

MTCSASSSVSYMHWYQQKSGTSPKRWIYDTSKLAS

GVPDRFSGSGSGTSYFLTINNMEAEDAATYYCQQW

NINPLTFGAGTKLELKRSDPTTTPAPRPPTPAPTI
```

-continued

ASQPLSLRPEACRPAAGGAVHTRGLDFACDIYIWA

PLAGTCGVLLLSLVITLYCRSKRSRLLHSDYMNMT

PRRPGPTRKHYQPYAPPRDFAAYRSRVKFSRSADA

PAYQQGQNQLYNELNLGRREEYDVLDKRRGRDPEM

GGKPRRKNPQEGLYNELQKDKMAEAYSEIGMKGER

RRGKGHDGLYQGLSTATKDTYDALHMQALPPR

Third generation CD19 CAR
                              SEQ ID No. 13
MGTSLLCWMALCLLGADHADAQVQLQQSGPELVKP

GASVKISCKASGYAFSSSWMNWVKQRPGKGLEWIG

RIYPGDEDTNYSGKFKDKATLTADKSSTTAYMQLS

SLTSEDSAVYFCARSLLYGDYLDYWGQGTTLTVSS

GGGGSGGGGSGGGGSQIVLTQSPAIMSASPGEKVT

MTCSASSSVSYMHWYQQKSGTSPKRWIYDTSKLAS

GVPDRFSGSGSGTSYFLTINNMEAEDAATYYCQQW

NINPLTFGAGTKLELKRSDPTTTPAPRPPTPAPTI

ASQPLSLRPEACRPAAGGAVHTRGLDFACDIFWVL

VVVGGVLACYSLLVTVAFIIFWVRSKRSRLLHSDY

MNMTPRRPGPTRKHYQPYAPPRDFAAYRSRDQRLP

PDAHKPPGGGSFRTPIQEEQADAHSTLAKIRVKFS

RSADAPAYQQGQNQLYNELNLGRREEYDVLDKRRG

RDPEMGGKPRRKNPQEGLYNELQKDKMAEAYSEIG

MKGERRRGKGHDGLYQGLSTATKDTYDALHMQALP

PR

CD19 CAR with IgG1 hinge spacer
                              SEQ ID No. 14
MGTSLLCWMALCLLGADHADAQVQLQQSGPELVKP

GASVKISCKASGYAFSSSWMNWVKQRPGKGLEWIG

RIYPGDEDTNYSGKFKDKATLTADKSSTTAYMQLS

SLTSEDSAVYFCARSLLYGDYLDYWGQGTTLTVSS

GGGGSGGGGSGGGGSQIVLTQSPAIMSASPGEKVT

MTCSASSSVSYMHWYQQKSGTSPKRWIYDTSKLAS

GVPDRFSGSGSGTSYFLTINNMEAEDAATYYCQQW

NINPLTFGAGTKLELKRSDPAEPKSPDKTHTCPPC

PKDPKFWVLVVVGGVLACYSLLVTVAFIIFWVRSK

RSRLLHSDYMNMTPRRPGPTRKHYQPYAPPRDFAA

YRSRVKFSRSADAPAYQQGQNQLYNELNLGRREEY

DVLDKRRGRDPEMGGKPRRKNPQEGLYNELQKDKM

AEAYSEIGMKGERRRGKGHDGLYQGLSTATKDTYD

ALHMQALPPR

-continued

CD19 CAR with hinge-CH2-CH3 of human
IgG1 with FcR binding sites mutated out
                              SEQ ID No. 15
MGTSLLCWMALCLLGADHADAQVQLQQSGPELVKP

GASVKISCKASGYAFSSSWMNWVKQRPGKGLEWIG

RIYPGDEDTNYSGKFKDKATLTADKSSTTAYMQLS

SLTSEDSAVYFCARSLLYGDYLDYWGQGTTLTVSS

GGGGSGGGGSGGGGSQIVLTQSPAIMSASPGEKVT

MTCSASSSVSYMHWYQQKSGTSPKRWIYDTSKLAS

GVPDRFSGSGSGTSYFLTINNMEAEDAATYYCQQW

NINPLTFGAGTKLELKRSDPAEPKSPDKTHTCPPC

PAPPVAGPSVFLFPPKPKDTLMIARTPEVTCVVVD

VSHEDPEVKFNWYVDGVEVHNAKTKPREEQYNSTY

RVVSVLTVLHQDWLNGKEYKCKVSNKALPAPIEKT

ISKAKGQPREPQVYTLPPSRDELTKNQVSLTCLVK

GFYPSDIAVEWESNGQPENNYKTTPPVLDSDGSFF

LYSKLTVDKSRWQQGNVFSCSVMHEALHNHYTQKS

LSLSPGKKDPKFWVLVVVGGVLACYSLLVTVAFII

FWVRSKRSRLLHSDYMNMTPRRPGPTRKHYQPYAP

PRDFAAYRSRVKFSRSADAPAYQQGQNQLYNELNL

GRREEYDVLDKRRGRDPEMGGKPRRKNPQEGLYNE

LQKDKMAEAYSEIGMKGERRRGKGHDGLYQGLSTA

TKDTYDALHMQALPPR

The CAR of the invention may comprise a variant of the sequence shown as SEQ ID No. 7, 8, 9, 10, 11, 12, 13, 14 or 15 having at least 80, 85, 90, 95, 98 or 99% sequence identity, provided that the variant sequence retain the capacity to bind CD19 (when in conjunction with a complementary VL or VH domain, if appropriate).

The percentage identity between two polypeptide sequences may be readily determined by programs such as BLAST which is freely available at http://blast.ncbi.nlm-.nih.gov.

Transmembrane Domain

The CAR of the invention may also comprise a transmembrane domain which spans the membrane. It may comprise a hydrophobic alpha helix. The transmembrane domain may be derived from CD28, which gives good receptor stability.

The transmembrane domain may comprise the sequence shown as SEQ ID No. 22.

SEQ ID No. 22
FWVLVVVGGVLACYSLLVTVAFIIFWV

Intracellular T Cell Signaling Domain (Endodomain)

The endodomain is the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, endodomains from CD28, or OX40 or 41BB can be used with CD3-Zeta to transmit a proliferative/survival signal, or all three can be used together.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains were constructed. Fusion of the intracellular part of a T-cell co-stimulatory molecule to that of CD3ζ resulted in second generation receptors which could transmit an activating and co-stimulatory signal simultaneously after antigen recognition. The co-stimulatory domain most commonly used was that of CD28. This supplies the most potent co-stimulatory signal, namely immunological signal 2, which triggers T-cell proliferation. Some receptors were also described which included TNF receptor family endodomains such as OX40 and 41BB which transmit survival signals. Finally, even more potent third generation CARs were described which had endodomains capable of transmitting activation, proliferation and survival signals. CARs and their different generations are summarized in FIG. 4.

The endodomain of the CAR of the present invention may comprise combinations of one or more of the CD3-Zeta endodomain, the 41BB endodomain, the OX40 endodomain or the CD28 endodomain.

The intracellular T-cell signalling domain (endodomain) of the CAR of the present invention may comprise the sequence shown as SEQ ID No. 23, 24, 25, 26, 27, 28, 29 or 30 or a variant thereof having at least 80% sequence identity.

```
(CD3 zeta endodomain)
                                 SEQ ID No. 23
RSRVKFSRSADAPAYQQGQNQLYNELNLGRREEYD

VLDKRRGRDPEMGGKPRRKNPQEGLYNELQKDKMA

EAYSEIGMKGERRRGKGHDGLYQGLSTATKDTYDA

LHMQALPPR (41BB endodomain)
                                 SEQ ID No. 24
KRGRKKLLYIFKQPFMRPVQTTQEEDGCSCRFPEEEEGGCEL (OX40 endodomain)
                                 SEQ ID No. 25
RRDQRLPPDAHKPPGGGSFRTPIQEEQADAHSTLAKI (CD28 endodomain)
                                 SEQ ID No. 26
KRSRLLHSDYMNMTPRRPGPTRKHYQPYAPPRDFAAY Examples of combinations of such endodomains
include 41BB-Z, OX40-Z, CD28-Z
and CD28-OX40-Zeta.
(41BB-Z endodomain fusion)
                                 SEQ ID No. 27
KRGRKKLLYIFKQPFMRPVQTTQEEDGCSCRFPEE

EEGGCELRVKFSRSADAPAYQQGQNQLYNELNLGR

REEYDVLDKRRGRDPEMGGKPRRKNPQEGLYNELQ

KDKMAEAYSEIGMKGERRRGKGHDGLYQGLSTATK

DTYDALHMQALPPR
```

```
                        -continued
(OX40-Z endodomain fusion)
                                 SEQ ID No. 28
RRDQRLPPDAHKPPGGGSFRTPIQEEQADAHSTLA

KIRVKFSRSADAPAYQQGQNQLYNELNLGRREEYD

VLDKRRGRDPEMGGKPRRKNPQEGLYNELQKDKMA

EAYSEIGMKGERRRGKGHDGLYQGLSTATKDTYDA

LHMQALPPR (CD28Z endodomain fusion)
                                 SEQ ID No. 29
KRSRLLHSDYMNMTPRRPGPTRKHYQPYAPPRDFA

AYRSRVKFSRSADAPAYQQGQNQLYNELNLGRREE

YDVLDKRRGRDPEMGGKPRRKNPQEGLYNELQKDK

MAEAYSEIGMKGERRRGKGHDGLYQGLSTATKDTY

DALHMQALPPR (CD28OXZ)
                                 SEQ ID No. 30
KRSRLLHSDYMNMTPRRPGPTRKHYQPYAPPRDFA

AYRSRDQRLPPDAHKPPGGGSFRTPIQEEQADAHS

TLAKIRVKFSRSADAPAYQQGQNQLYNELNLGRRE

EYDVLDKRRGRDPEMGGKPRRKNPQEGLYNELQKD

KMAEAYSEIGMKGERRRGKGHDGLYQGLSTATKDT

YDALHMQALPPR
```

A variant sequence may have at least 80%, 85%, 90%, 95%, 98% or 99% sequence identity to SEQ ID No. 22, 23, 24, 25, 26, 27, 28, 29 or 30 provided that the sequence provides an effective transmembrane domain/intracellular T cell signaling domain.

Signal Peptide

The CAR of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The CAR of the invention may have the general formula:

Signal peptide—CD19-binding domain—spacer domain—transmembrane domain/intracellular T cell signaling domain.

The signal peptide may comprise the SEQ ID No. 31 or a variant thereof having 5, 4, 3, 2 or 1 amino acid mutations (insertions, substitutions or additions) provided that the signal peptide still functions to cause cell surface expression of the CAR.

SEQ ID No. 31:
          METDTLLLWVLLLVPGSTG

The signal peptide of SEQ ID No. 31 is compact and highly efficient. It is predicted to give about 95% cleavage after the terminal glycine, giving efficient removal by signal peptidase.

Spacer

The CAR of the present invention may comprise a spacer sequence to connect the CD19-binding domain with the transmembrane domain and spatially separate the CD19-binding domain from the endodomain. A flexible spacer allows to the CD19-binding domain to orient in different directions to enable CD19 binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

```
SEQ ID No. 32 (hinge-CH2CH3 of human IgG1)
AEPKSPDKTHTCPPCPAPPVAGPSVFLFPPKPKDT

LMIARTPEVTCVVVDVSHEDPEVKFNWYVDGVEVH

NAKTKPREEQYNSTYRVVSVLTVLHQDWLNGKEYK

CKVSNKALPAPIEKTISKAKGQPREPQVYTLPPSR

DELTKNQVSLTCLVKGFYPSDIAVEWESNGQPENN

YKTTPPVLDSDGSFFLYSKLTVDKSRWQQGNVFSC

SVMHEALHNHYTQKSLSLSPGKKD

SEQ ID No. 33 (human CD8 stalk):
TTTPAPRPPTPAPTIASQPLSLRPEACRPAAGGA

VHTRGLDFACDI

SEQ ID No. 34 (human IgG1 hinge):
AEPKSPDKTHTCPPCPKDPK

SEQ ID No. 35 (IgG1 Hinge-Fc)
AEPKSPDKTHTCPPCPAPELLGGPSVFLFPPKPKD

TLMISRTPEVTCVVVDVSHEDPEVKFNWYVDGVEV

HNAKTKPREEQYNSTYRVVSVLTVLHQDWLNGKEY

KCKVSNKALPAPIEKTISKAKGQPREPQVYTLPPS

RDELTKNQVSLTCLVKGFYPSDIAVEWESNGQPEN

NYKTTPPVLDSDGSFFLYSKLTVDKSRWQQGNVFS

CSVMHEALHNHYTQKSLSLSPGKKDPK

SEQ ID No. 36
(IgG1 Hinge-Fc modified to remove Fc
receptor recognition motifs)
AEPKSPDKTHTCPPCPAPPVA*GPSVFLFPPKPKD

TLMIARTPEVTCWVDVSHEDPEVKFNWYVDGVEVH
```

```
-continued

NAKTKPREEQYNSTYRVVSVLTVLHQDWLNGKEYK

CKVSNKALPAPIEKTISKAKGQPREPQVYTLPPSR

DELTKNQVSLTCLVKGFYPSDIAVEWESNGQPENN

YKTTPPVLDSDGSFFLYSKLTVDKSRWQQGNVFSC

SVMHEALHNHYTQKSLSLSPGKKDPK
Modified residues are underlined; * denotes a deletion.
```

Interferon Release and CAR T-Cell Exhaustion

The present inventors have found that a CD19 CAR based on the CAT19 scFv has properties which may result in lower toxicity and better efficacy.

Given that the main experience with CD19 CAR therapy has been with CARs based on the fmc63 scFv, and that the oldest, largest and perhaps most significant clinical data set is with the fmc63 based Campana CAR, the present inventors took this Campana CAR as the "gold-standard". A comparison was hence made between the fmc63-Campana CAR and a similar CAR but with CAT19 scFv instead of fmc63. Surprisingly, the present inventors found that while CAT19 CAR T-cells effected killing of target cell expressing CD19, and proliferated in response to CD19 expressing targets, Interferon-gamma release was less. Further, a small animal model of an aggressive B-cell lymphoma showed equal efficacy and equal engraftment between the fmc63 and CAT19 based CARs, but surprisingly, less of the CAT19 CAR T-cells were exhausted than fmc63 CAR T-cells.

The CAR of the invention may cause 25, 50, 70 or 90% lower IFNγ release in a comparative assay involving bringing CAR T cells into contact with target cells.

The CAR of the invention may result in a smaller proportion of CAR T cells becoming exhausted than fmc63 CAR T cells. T cell exhaustion may be assessed using methods known in the art, such as analysis of PD-1 expression. The CAR of the present invention may cause 20, 30, 40, 50, 60 of 70% fewer CAR T cells to express PD-1 that fmc63 CAR T cells in a comparative assay involving bringing CAR T cells into contact with target cells.

Nucleic Acid Sequence

The second aspect of the invention relates to a nucleic acid sequence which codes for a CAR of the first aspect of the invention.

The nucleic acid sequence may be capable of encoding a CAR having the amino acid sequence shown as any of SEQ ID No. 10-15.

Vector

The present invention also provides a vector which comprises a nucleic acid sequence according to the present invention. Such a vector may be used to introduce the nucleic acid sequence into a host cell so that it expresses and produces a molecule according to the first aspect of the invention.

The vector may, for example, be a plasmid or a viral vector, such as a retroviral vector or a lentiviral vector.

The vector may be capable of transfecting or transducing a cell, such as a T cell.

Cell

The invention also provides a cell which comprises a nucleic acid according to the invention. The invention provides a cell which expresses a CAR according to the first aspect of the invention at the cell surface.

The cell may be a cytolytic immune cell, such as a T-cell or natural killer (NK) cell.

A cell capable of expressing a CAR according to the invention may be made by transducing or transfecting a cell with CAR-encoding nucleic acid.

The CAR-expressing cell of the invention may be generated ex vivo. The cell may be from a cell sample, such as a peripheral blood mononuclear cell (PBMC) sample from the patient or a donor. Cells may be activated and/or expanded prior to being transduced with CAR-encoding nucleic acid, for example by treatment with an anti-CD3 monoclonal antibody.

Pharmaceutical Composition

The present invention also relates to a pharmaceutical composition containing a CAR-expressing cell, or plurality of cells, of the invention together with a pharmaceutically acceptable carrier, diluent or excipient, and optionally one or more further pharmaceutically active polypeptides and/or compounds. Such a formulation may, for example, be in a form suitable for intravenous infusion.

Method of Treatment

CAR-expressing cells of the present invention may be capable of killing cancer cells, such as B-cell lymphoma cells. CAR-expressing cells, such as T-cells or NK cells, may either be created ex vivo either from a patient's own peripheral blood (1$^{st}$ party), or in the setting of a haematopoietic stem cell transplant from donor peripheral blood (2$^{nd}$ party), or peripheral blood from an unconnected donor (3$^{rd}$ party). Alternatively, CAR-expressing cells may be derived from ex vivo differentiation of inducible progenitor cells or embryonic progenitor cells to cells such as T-cells. In these instances, CAR cells are generated by introducing DNA or RNA coding for the CAR by one of many means including transduction with a viral vector, transfection with DNA or RNA.

T or NK cells expressing a CAR molecule of the present invention may be used for the treatment of a cancerous disease, in particular a cancerous disease associated with CD19 expression.

A method for the treatment of disease relates to the therapeutic use of a cell or population of cells of the invention. In this respect, the cells may be administered to a subject having an existing disease or condition in order to lessen, reduce or improve at least one symptom associated with the disease and/or to slow down, reduce or block the progression of the disease. The method of the invention may cause or promote cell mediated killing of CD19-expressing cells, such as B cells.

The invention will now be further described by way of Examples, which are meant to serve to assist one of ordinary skill in the art in carrying out the invention and are not intended in any way to limit the scope of the invention.

EXAMPLES

Example 1—Cloning of VH and VL and Demonstration of CD19 Binding

The VH and VL were cloned from a mouse anti-CD19 monoclonal antibody and fused in frame with the human kappa constant region and the human IgG1 constant region. These chimeric heavy and light chains were cloned into an expression vector and used to transfect 293T cells. The subsequent produced antibody was used to stain SupT1 cells (a T-cell line which is CD19 negative), and SupT1 cells which have been engineered to be CD19 positive. This staining shows specific binding of the CD19 (FIG. 2).

Example 2—Demonstration that the VH/VL can Form an scFv which Binds CD19

It was then investigated whether the cloned VH and VL could bind CD19 in a scFv format. The VH and VL were cloned as an scFv in two orientations: VH-VL and VL-VH, where the two variable regions were separated by a linker comprising of (SGGGG)4. These scFv were cloned into a non-signalling CAR co-expressed with truncated CD34 as shown in FIG. 3a. Briefly, this comprises of a signal peptide, scFv, hinge-CH2-CH3 of human IgG1, the CD8 transmembrane domain, the first 12 residues of the CD8 endodomain, a FMD-2A peptide TeV, truncated human CD34. To allow comparison, scFv from fmc63, and scFv from another anti-CD19 hybridoma 4g7, were cloned in the same format in both VH-VL and VL-VH orientations.

In this way, several parameters can be studied: (1) the binding of target antigen to the CAR by use of recombinant cognate target antigen fused to murine Fc, unencumbered by internalization of the receptor due to signalling; (2) The stability of the receptor can be determined using polyclonal anti-Fc; (3) the expression levels of the cassette can be controlled for by co-staining for CD34.

These constructs were transduced into SupT1 cells. Recombinant CD19-mouse IgG2aFc fusion was generated. SupT1 cells were stained for mouse-Fc, human-Fc and anti-CD34 with antibodies conjugated to different fluorophores and stability/binding interrogated by flow-cytometery.

The sequences of the different scFvs used are detailed below:

```
>scFv_fmc63_VH-VL
                              (SEQ ID No. 37)
EVKLQESGPGLVAPSQSLSVTCTVSGVSLPDYGVS

WIRQPPRKGLEWLGVIWGSETTYYNSALKSRLTII

KDNSKSQVFLKMNSLQTDDTAIYYCAKHYYYGGSY

AMDYWGQGTSVTVSSGGGGSGGGGSGGGGSDIQMT

QTTSSLSASLGDRVTISCRASQDISKYLNWYQQKP

DGTVKLLIYHTSRLHSGVPSRFSGSGSGTDYSLTI

SNLEQEDIATYFCQQGNTLPYTFGGGTKLEITKA

>scFv_fmc63_VL-VH
                              (SEQ ID No. 38)
DIQMTQTTSSLSASLGDRVTISCRASQDISKYLNW

YQQKPDGTVKLLIYHTSRLHSGVPSRFSGSGSGTD

YSLTISNLEQEDIATYFCQQGNTLPYTFGGGTKLE

ITKAGGGGSGGGGSGGGGSEVKLQESGPGLVAPSQ

SLSVTCTVSGVSLPDYGVSWIRQPPRKGLEWLGVI

WGSETTYYNSALKSRLTIIKDNSKSQVFLKMNSLQ

TDDTAIYYCAKHYYYGGSYAMDYWGQGTSVTVSS

>scFv_4g7_VH-VL
                              (SEQ ID No. 39)
EVQLQQSGPELIKPGASVKMSCKASGYTFTSYVMH

WVKQKPGQGLEWIGYINPYNDGTKYNEKFKGKATL
```

```
                    -continued

TSDKSSSTAYMELSSLTSEDSAVYYCARGTYYYGS

RVFDYWGQGTTLTVSSGGGGSGGGGSGGGGSDIVM

TQAAPSIPVTPGESVSISCRSSKSLLNSNGNTYLY

WFLQRPGQSPQLLIYRMSNLASGVPDRFSGSGSGT

AFTLRISRVEAEDVGVYYCMQHLEYPFTFGAGTKL

ELKR

>scFv_4g7_VL-VH
                                (SEQ ID No. 40)
DIVMTQAAPSIPVTPGESVSISCRSSKSLLNSNGN

TYLYWFLQRPGQSPQLLIYRMSNLASGVPDRFSGS

GSGTAFTLRISRVEAEDVGVYYCMQHLEYPFTFGA

GTKLELKRSGGGGSGGGGSGGGGSEVQLQQSGPEL

IKPGASVKMSCKASGYTFTSYVMHWVKQKPGQGLE

WIGYINPYNDGTKYNEKFKGKATLTSDKSSSTAYM

ELSSLTSEDSAVYYCARGTYYYGSRVFDYWGQGTT

LTVSS

>scFv_CAT_VH-VL
                                (SEQ ID No. 9)
QVQLQQSGPELVKPGASVKISCKASGYAFSSSWMN

WVKQRPGKGLEWIGRIYPGDEDTNYSGKFKDKATL

TADKSSTTAYMQLSSLTSEDSAVYFCARSLLYGDY

LDYWGQGTTLTVSSGGGGSGGGGSGGGGSQIVLTQ

SPAIMSASPGEKVTMTCSASSSVSYMHWYQQKSGT

SPKRWIYDTSKLASGVPDRFSGSGSGTSYFLTINN

MEAEDAATYYCQQWNINPLTFGAGTKLELKR

>scFv_CAT_VL-VH
                                (SEQ ID No. 41)
QIVLTQSPAIMSASPGEKVTMTCSASSSVSYMHWY

QQKSGTSPKRWIYDTSKLASGVPDRFSGSGSGTSY

FLTINNMEAEDAATYYCQQWNINPLTFGAGTKLEL

KRSGGGGSGGGGSGGGGSQVQLQQSGPELVKPGAS

VKISCKASGYAFSSSWMNWVKQRPGKGLEWIGRIY

PGDEDTNYSGKFKDKATLTADKSSTTAYMQLSSLT

SEDSAVYFCARSLLYGDYLDYWGQGTTLTVSS
```

The construct used and the staining results are summarized in FIG. 3. Surprisingly, the CAT CAR with scFv in VH-VL orientation binds CD19, while the CAT19 CAR with scFv in the VL-VH orientation gave minimal CD19 binding. This was in contrast to the fmc63 CARs and 4g7 CARs which bound CD19 in both the HL and LH orientations. Binding and stability of the HL CAT CAR appeared equal to that with fmc63.

Example 3—In Vitro Comparison of CAT19 CAR Function Against Fmc36 CAR

The CAT scFv in HL orientation was cloned into a CAR scaffold designed by Campana (Imai et al (2004) Leuk. Off. J. Leuk. Soc, Am. Leuk, Res. Fund. UK 18:676-684). Effectively the fmc63 scFv was replaced with a CAT scFv, and compared with the original fmc63 based CAR. This CAR comprises a signal peptide, the scFv, a CD8 stalk spacer and transmembrane and 41BB and Zeta endodomains. The amino acid sequences of the CAT CAR and fmc63 CAR are given below:

```
>CAT19_CAR
                                (SEQ ID No. 10)
MGTSLLCWMALCLLGADHADAQVQLQQSGPELVKP

GASVKISCKASGYAFSSSWMNWVKQRPGKGLEWIG

RIYPGDEDTNYSGKFKDKATLTADKSSTTAYMQLS

SLTSEDSAVYFCARSLLYGDYLDYWGQGTTLTVSS

GGGGSGGGGSGGGGSQIVLTQSPAIMSASPGEKVT

MTCSASSSVSYMHWYQQKSGTSPKRWIYDTSKLAS

GVPDRFSGSGSGTSYFLTINNMEAEDAATYYCQQW

NINPLTFGAGTKLELKRSDPTTTPAPRPPTPAPTI

ASQPLSLRPEACRPAAGGAVHTRGLDFACDIYIWA

PLAGTCGVLLLSLVITLYCKRGRKKLLYIFKQPFM

RPVQTTQEEDGCSCRFPEEEEGGCELRVKFSRSAD

APAYQQGQNQLYNELNLGRREEYDVLDKRRGRDPE

MGGKPRRKNPQEGLYNELQKDKMAEAYSEIGMKGE

RRRGKGHDGLYQGLSTATKDTYDALHMQALPPR

>Fmc63_CAR, as described by Imai et al
(2004) as above
                                (SEQ ID No. 42)
METDTLLLWVLLLWVPGSTGDIQMTQTTSSLSASL

GDRVTISCRASQDISKYLNWYQQKPDGTVKLLIYH

TSRLHSGVPSRFSGSGSGTDYSLTISNLEQEDIAT

YFCQQGNTLPYTFGGGTKLEITKAGGGGSGGGGSG

GGGSGGGGSEVKLQESGPGLVAPSQSLSVTCTVSG

VSLPDYGVSWIRQPPRKGLEWLGVIWGSETTYYNS

ALKSRLTI IKDNSKSQVFLKMNSLQTDDTAIYYC

AKHYYYGGSYAMDYWGQGTSVTVSSDPTTTPAPRP

PTPAPTIASQPLSLRPEACRPAAGGAVHTRGLDFA

CDIYIWAPLAGTCGVLLLSLVITLYCKRGRKKLLY

IFKQPFMRPVQTTQEEDGCSCRFPEEEEGGCELRV

KFSRSADAPAYQQGQNQLYNELNLGRREEYDVLDK

RRGRDPEMGGKPRRKNPQEGLYNELQKDKMAEAYS

EIGMKGERRRGKGHDGLYQGLSTATKDTYDALHMQ

ALPPR
```

Primary human T-cells from 5 different donors were transduced with lentiviral vectors coding for CAT19 CAR in Campana format, or the fmc63 Campana CAR itself. These T-cells were then used in various assays. Chromium release assay was performed against SupT1 cells. These cells are CD19 negative. Neither CAR T-cells responded against this cell line demonstrating that CAR19 CAR has no non-specific killing activity against CD19 negative cells [FIG. 5(a)]. (b) Chromium release assay was also performed against SupT1 cells engineering to express CD19. Both CARs performed equally against this cell line in this assay with high-levels of killing [FIG. 5(b)]. Next a degranulation assay was performed by staining for CD107 on the surface of effector cells after co-culture with target cells. Here either NT T-cells, fmc63 CAR T-cells, or CAT19 CAR T-cells were used as effectors and either SupT1 or SupT1.CD19 cells were used as targets. Surface CD107 was detected by flow-cytometry which allowed differential measurement of degranulation of CD4+ and CD8+ cells. [FIGS. 5(c) and (d) respectively]. Degranulation was increased with CAT19 CAR T-cells in comparison with fmc63 CAR T-cells. Pro-liferation was estimated using tritiated thymidilate incorpo-ration. Here, NT, fmc63 CAR T-cells, CAT19 CAR T-cells were co-cultured with SupT1 cells engineered to express CD19. Incorporation of thymidiln this experiment, an irrel-evant CAR targeting GD2 was also tested. There was a trend to increased proliferation with CAR19 CAR T-cells [FIG. 4(e)]. Next, interferon-gamma release from either NT T-cells, fmc63 CAR T-cells, CAT19 CAR T-cells or GD2 CAR T-cells 24 hours after challenge against SupT1 or SupT1.CD19 cells was measured by ELISA. CAT19 CAR T-cells produced significantly less interferon-gamma than fmc63 CAR T-cells when challenged with CD19+ targets.

Example 4—Demonstration of In Vivo Efficacy of CAT19 CAR Therapy

An outline of experimental set-up for this in vivo model is present in FIG. 6(a). Briefly NSG (NOD scid gamma, NOD.Cg-Prkdc$^{scid}$ Il2rg$^{tm1Wjl}$/SzJ) mice are sufficiently immunocompromised that they are permissive for engraft-ment of human cell lines and primary human T-cells. Raji cells are a B-cell line derived from Burkitt's lymphoma. These cells readily engraft within the bone-marrow of NSG mice causing an aggressive leukaemia-like syndrome. Raji cells were engineered to express fire-fly Luciferase to allow non-invasive tracking using bioluminescence imaging (BLI). Mice were injected with 2.5×10^5 Raji.FLuc cells via tail vein injection. 24 hours later 4×10^6 of either NT primary human T-cells, or T-cells transduced with fmc63 CAR, or T-cells transduced with CAT19 CAR were admin-istered via tail-vein. Tumour response was measured sequentially by BLI. Tail-vein blood was sampled at day 4 for engraftment and serum cytokine. The animals were culled at day 11 and tissues studied for persistence of CAR T-cells and tumour burden. BLI imaging of the different mouse cohorts at day 10 is shown in FIG. 6(b). Extensive disease is seen in the pelvis, spine, ribs, skull and spleen of mice treated with NT T-cells, while minimal signal is evident in mice who received either CAT19 CAR T-cells, or fmc63 CAR T-cells. Quantitative bioluminescent signal averaged from different mouse cohorts over time is shown on a log-scale in FIG. 6(c). A clear difference is seen between signal accumulation in mice who received NT T-cells, and mice who received CAR T-cells. No difference in signal accumulation is seen in mice who received fmc63 CAR T-cells or CAT19 CAR T-cells. Finally, after sacrifice, flow-cytometric analysis of bone-marrow from each mouse was performed to directly determine tumour burden. Raji cells are easily distinguishable from mouse haematopoietic cells and from adoptively transferred T-cells, since they express human B-cell markers. Minimal Raji cells could be detected in marrow of mice who received either fmc63 or CAT19 CAR T-cells.

Example 5—Characterization of In Vivo Persisting CAR T-Cells

From the above animal models, the present inventors sought to determine if both types of CAR T-cells engrafted within the bone-marrow and spleen of these NSG mice. Flow-cytometric analysis of bone-marrow and spleen with counting beads allowed determination of absolute numbers of CAR T-cells. This data is shown in FIGS. 7(a) and (b). The absolute numbers of CAR T-cells in spleens of mice from animals treated with fmc63 CAR T-cells or CAT19 CAR T-cells was similar. Next, the present inventors pro-ceeded to determine if there was any difference in the numbers of exhausted T-cells in these different tissues. By co-staining for PD1 expression in the above samples the numbers of exhausted T-cells could be determined. This data is shown in FIGS. 7(c) and (d). Surprisingly, fewer exhausted T-cells were present in both tissue compartments with the CAT19 CAR than the fmc63 CAR.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be under-stood that the invention as claimed should not be unduly limited to such specific embodiments. Indeed, various modi-fications of the described modes for carrying out the inven-tion which are obvious to those skilled in molecular biology, CAR technology or related fields are intended to be within the scope of the following claims.

---

The invention claimed is:

1. A chimeric antigen receptor (CAR) comprising the amino acid sequence of SEQ ID NO: 10.

2. A cell that comprises the CAR according to claim 1.

3. The cell according to claim 2 that is a hematopoietic stem cell or progenitor cell.

4. The cell according to claim 2 that is a T cell or a natural killer (NK) cell.

5. A composition that comprises a plurality of cells according to claim 2.

6. The composition according to claim 5, further comprising a pharmaceutically acceptable carrier.

7. A composition that comprises a plurality of cells according to claim 3.

8. The composition according to claim 7, further comprising a pharmaceutically acceptable carrier.

9. A composition that comprises a plurality of cells according to claim 4.

10. The composition according to claim 9, further comprising a pharmaceutically acceptable carrier.

11. A method for making a cell according to claim 2, which comprises the step of transducing or transfecting a cell with a vector that comprises a nucleotide sequence that encodes a CAR that comprises the amino acid sequence of SEQ ID NO: 10.

12. The method according to claim 11, wherein the cell is a T cell or NK cell.

13. The method according to claim 11, wherein the cell is a hematopoietic stem cell or progenitor cell.

14. A nucleic acid comprising a nucleotide sequence that encodes a chimeric antigen receptor (CAR), said CAR comprising the amino acid sequence of SEQ ID NO: 10.

15. A vector that comprises the nucleic acid according to claim 14.

* * * * *